(12) United States Patent
Keler et al.

(10) Patent No.: US 6,682,928 B2
(45) Date of Patent: *Jan. 27, 2004

(54) CELLS EXPRESSING ANTI-FC RECEPTOR BINDING COMPONENTS

(75) Inventors: Tibor Keler, Ottsville, PA (US); Joel Goldstein, Piscataway, NJ (US); Robert Graziano, Frenchtown, NJ (US); Yashwant M. Deo, Audubon, PA (US)

(73) Assignee: Medarex, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 9 days.

(21) Appl. No.: 09/203,958

(22) Filed: Dec. 2, 1998

(65) Prior Publication Data

US 2003/0039641 A1 Feb. 27, 2003

Related U.S. Application Data

(60) Provisional application No. 60/067,232, filed on Dec. 2, 1997.

(51) Int. Cl.$^7$ .................. C12N 15/63; C12N 15/00; C12N 15/74; A61K 48/00

(52) U.S. Cl. .............. 435/325; 435/320.1; 435/326; 435/328; 435/324; 435/455; 435/93.1; 435/93.21; 514/44

(58) Field of Search .............. 435/320.1, 325, 435/326, 328, 334, 455; 424/93.21, 455, 93.1; 514/44

(56) References Cited

U.S. PATENT DOCUMENTS

| | | | |
|---|---|---|---|
| 4,470,925 A | 9/1984 | Auditore-Hargreaves | ... 260/112 B |
| 4,676,980 A | 6/1987 | Segal et al. | ................. 424/85 |
| 4,954,617 A | 9/1990 | Fanger et al. | ............... 530/387 |
| 5,635,600 A | 6/1997 | Fanger et al. | ........... 530/387.3 |

FOREIGN PATENT DOCUMENTS

| | | | |
|---|---|---|---|
| DE | 19634159 | | 9/1997 |
| WO | WO 91/00360 | * | 1/1991 |
| WO | WO 91/05871 | | 5/1991 |
| WO | WO 91/03493 | | 3/1992 |
| WO | WO 92/05793 | | 4/1992 |
| WO | WO 92/10591 | | 6/1992 |
| WO | WO 92/15322 | | 9/1992 |
| WO | WO 94/10332 | | 5/1994 |
| WO | WO 95/09917 | | 4/1995 |
| WO | WO 96/40789 | | 12/1996 |
| WO | WO 97/07218 | | 2/1997 |
| WO | WO 97/20048 | * | 6/1997 |
| WO | WO 97/35004 | | 9/1997 |

OTHER PUBLICATIONS

Guyre et al. (1997) Canc. Immunol. Immunother., vol. 45, 146–148, 1997.*
Daeron et al. (1997) Annu. Rev. Immunol., vol. 15, 203–234, 1997.*
Miller et al. (1995) FASEB, vol. 9, 190–199, 1995.*
Deonarain et al. (1998) Exp. Opin. Ther. Patents, vol. 8 (1), 53–69, 1998.*
Anderson, C. et al. (1986) "Stimulation of Superoxide Production by a Monoclonal Antibody (mab) Against the High Affinity IgG Fc Receptor (FcRI) of U937 Cells", *Fed. Proc., 45:* 714, Abstract #3247.
Ball, E. et al. (1992) "Initial Trial of Bispecific Antibody–Mediated Immunotherapy of CD15–Bearing Tumors: Cytotoxicity of Human Tumor Cells Using a Bispecific Antibody Comprised of Anti–CD15 (MoAb PM81) and Anti–CD64/FcγRI (MoAb32)", *J. of Hematotherapy, 1*:85–94.
Brennan, M. et al. (1985) "Preparation of Bispecific Antibodies by Chemical Recombination of Monoclonal Immunoglobulin G$_1$ Fragments", *Science, 229:* 81–83.
Chang, T. W. (1985) "Regulation of immune response by antibodies: the importance of antibody and monocyte Fc receptor interaction in T cell activation", *Immun. Today,* 6:245.
Chen, J. et al. (1985) "An Immunoconjugate of Lys3–Bombesin and Monoclonal Antibody 22 Can Specifically Induce FcgammaRI (CD64)–Dependent Monocyte– and Neutrophil–Mediated Lysis of Small Cell Carcinoma of the Lung Cells", *Clinical Cancer Research, 1* (4):425–434.
Clark, M. et al. (1990) "Use of Bispecific Monoclonal Antibodies to Treat Hematological Malignancies: A Model System Using CD3 Transgenic Mice", *Bispecific Antibodies and Targeted Cellular Cytotoxicity,* Edited by Romet–Lemonne et al., Fondation Nationale de Transfustion Sanguine, Les Ulis, France, pp. 243–247.
de Leij, L. et al. (1990) "Intrapleural and Intraperitoneal Application of Bispecific Antibody Retargeted Lymphocytes to Cancer Patients", *Bispecific Antibodies and Targeted Cellular Cytotoxicity,* Edited by Romet–Lemmone et al., Fondation Nationale de Transfusion Sanguine, Les Ulis, France, pp. 249–253.
de Palazzo, I. et al. (1990) "Potentiation of Tumor Lysis by a Bispecific Antibody that Binds to CA19–9 Antigen and the Fcγ Receptor Expressed by Human Large Granular Lymphocytes", *Cancer Research, 50*:7123–7128.

(List continued on next page.)

Primary Examiner—Anne M. Wehbe'
(74) Attorney, Agent, or Firm—Lahive & Cockfield, LLP; Giulio A. DeConti, Jr., Esq.; Jane E. Remillard, Esq.

(57) ABSTRACT

Cells transformed to express on their surface a component which binds to an Fc receptor of an effector cell are disclosed. Also disclosed are expression vectors used to transform the cells. Once transformed, the cells bind to effector cells via the Fc receptor of the effector cell to stimulate an effector cell mediated immune response.

24 Claims, 19 Drawing Sheets

OTHER PUBLICATIONS

Dillman, R. (1989) "Monoclonal Antibodies for Treating Cancer", *Annals of Interal Medicine, 111*:592–603.

Ericson, S. et al. (1994) "The Effect of Recombinant Human Interleukin–3 and Recombinant Human Granulocyte–macro–Phage Colony–Stimulating Factor on Fcγ Receptor Expression and Antibody–Dependent Cellular Cytotoxicity of Hematopoietic Progenitor Cells During in Vitro Myeloid Maturation", *Experimental Hematology, 22*:283–289.

Falo et al. (1995) "Targeting antigen into the phagocytic pathway in vivo induces protective tumor immunity", *Nat. Med. 1*:649.

Fanger, M. et al. (1994) "Production and Use of Anti–FcR Bispecific Antibodies" *Immunomethods 4* (1): 72–81.

Fanger, M. et al. (1992) "Fcγ Receptors in Cancer and Infectious Disease", *Immunol. Res., 11*:203–216.

Fanger, M. et al. (1992) "Bispecific Antibodies" *Critical Reviews in Immunology, 12* (3,4):101–124.

Gosselin et al. (1992) "Enhanced antigen presentation using human Fcg receptor (monocyte/macrophage)–specific immunogens", *J. Immun. 149*:3477.

Graziano, R. et al. (1995) "Construction and Characterization of a Humanized Anti–Gamma–Ig Receptor Type I (Fcgamma RI) Monoclonal Antibody" *The Journal of Immunology, 155* (10): 4996–5002.

Guyre, P. et al. (1989) "Monoclonal Antibodies that Bind to Distinct Epitopes on FcγRI are able to Trigger Receptor Function", *The Journal of Immunology, 143* (5), pp. 1650–1655.

Guyre, P. et al. (1983) "Recombinant Immune Interferon Increases Immunoglobulin G Fc Receptors on Cultured Human Mononuclear Phagocytes", *Journal of Clinical Investigation, 72*:393–397.

Harris, W. et al. (1993) "Therapeutic Antibodies—The Coming of Age", *Tibtech, 11*:42–44.

Hird, V. et al. (1990) "Immunotherapy with Monoclonal Antibodies", *Genes and Cancer*, Edited by D. Carney and K. Sikora, Chapter 17, pp. 183–189.

Isturiz, M. et al. (1991) "Two Different Fcγ Receptor–Dependent Cytotoxic Mechanisms Triggered by Monoclonal Immunoglobulins", *Immunology Letters, 29*:271–276.

Jung, Gundram, et al., 1991, "Target Cell–Induced T cell Activation with Bi– and Trispecific Antibody Fragments", *Eur. J. Immunol., 21*:2431–2435.

Karpovsky, B. et al. (1984) "Production of Target–Specific Effector Cells Using Hetero–Cross–Linked Aggregates Containing Anti–Target Cell and Anti–Fcγ Receptor Antibodies", *Journal of Experimental Medicine, 160*:1686–1701.

Kovacsovics–Bankowski et al. (1993) "Efficient major histocompatibility complex class I presentation of exogenous antigen upon phagocytosis by macrophages", *Proc. Natl. Acad. Sci. USA, 90*:4942.

Liu, M. et al. (1985) "Heteroantibody Duplexes Target Cells for Lysis by Cytotoxic T Lymphocytes", *PNAS, 82*:8648–8652.

Looney, R. et al. (1986) "Human Monocytes and U937 Cells Bear Two Distinct Fc Receptors for IgG", *The Journal of Immunology, 136* (5):1641–1647.

Lubeck, M. et al. (1985) "The Interaction of Murine IgG Subclass Proteins with Human Monocyte Fc Receptors", *The Journal of Immunology, 135* (2):1299–1304.

Mabondzo, A. et al. (1994) "Antibody–dependent Cellular Cytotoxicity and Neutralization of Human Immunodeficiency Virus Type 1 by High Affinity Corss–Linking of gp41 to Human Macrophage Fc IgG Receptor Using Bispecific Antibody", *Journal of Virology, 75*:1451–1456.

Nitta, T. et al. (1990) "Preliminary Trial of Specific Targeting Therapy Against Malignant Glioma", *The Lancet, 335*:368–376.

Perez, P. et al. (1985) "Specific Targeting of Cytotoxic T Cells by Anti–Target Cell Antibody", *Nature, 316*:354–356.

Repp, R. et al. (1994) "G–CSF Stimulated Neutrophils As Effector Cells In Immunotherapy With A Bispecific Antibody to FcgammaRI and To HER–2/neu (MDX210): Pre–clinical Studies", *Immunobiology, 191* (2–3): 250–251.

Sarmay, G. et al. (1992) "Mapping and Comparison of the Interaction Sites on The Fc Region of IgG Responsible for Triggering Antibody Dependent Cellular Cytotoxicity (ADCC) Through Different Types of Human Fcγ Receptor", *Molecular Immunology, 29* (5):633–639.

Schlom, J. (1991) "Monoclonal Antibodies: They're More and Less Than You Think", *Molecular Foundations of Biology* Edited by Williams and Wilkins, Chapter 6, pp. 95–134.

Shen, L. et al. (1984) "Direct Stimulation of ADCC by cloned Gamma Interferon is not Ablated by Glucocorticoids: Studies Using a Human Monocyte–like Cell Line (U–937)", *Molecular Immunology, 21* (2):167–173.

Shen, L. et al. (1986) "Heteroantibody–Mediated Cytotoxicity: Antibody to the High Affinity Fc Receptor for IgG Mediates Cytotoxicity by Human Monocytes that is Enhanced by Interferon–γ and is not Blocked by Human IgG", *The Journal of Immunology, 137* (11): 3378–3382.

Valerius, T. et al. (1993) "Involvement of the High–Affinity Receptor for IgG (FcγRI; CD64) in Enhanced Tumor Cell Cytotoxicity of Neutrophils During Granulocyte Colony–Stimulating Factor Therapy", *Blood, 82* (3): 931–393.

van de Winkel, J. et al. (1993) "Human IgG Fc Receptor Heterogeneity: Molecular Aspects and Clinical Implications", *Immunology Today, 14* (5): 215–221.

Waldmann, T. (1991) "Monoclonal Antibodies in Diagnosis and Therapy", *Science, 252*:1657–1662

* cited by examiner

Sequence Range: 1 to 1132

```
                              >BamHI
                              >BstYI
                         >BsiHKAI
                        >Bsp1286I
              >KpnI    >SacI              >BsiEI          >ApoI
          >Acc65I    >BanII    >SpeI    >EaeI           >EcoRI
 >HindIII   >BanI    >Ecl136II         >EagI         >BstXI
     |        |  10     |   20      |  30   |   40      |   50        60
     *        *  *      *   *       *  *    *   *       *   *         *
   AAGCTTGGTA CCGAGCTCGG ATCCACTAGT AACGGCCGCC AGTGTGCTGG AATTCGGCTT
   TTCGAACCAT GGCTCGAGCC TAGGTGATCA TTGCCGGCGG TCACACGACC TTAAGCCGAA >StyI
   >EcoRV    >NcoI
       |        |
       *   70   *   80         90         100         110
       *   *    *   *     *    *     *    *     *     *
   GGGGATATCC ACC ATG GAG ACA GAC ACA CTC CTG CTA TGG GTA CTG CTG CTC
   CCCCTATAGG TGG TAC CTC TGT CTG TGT GAG GAC GAT ACC CAT GAC GAC GAG
                  Met Glu Thr Asp Thr Leu Leu Leu Trp Val Leu Leu Leu>
               __c___c___c___c__IG K-CHAIN SP____c___c___c___c___>

>NdeI
          120        130        140   |   150        160
           *    *     *    *     *    *    *    *     *    *
   TGG GTT CCA GGT TCC ACT GGT GAC TAT CCA TAT GAT GTT CCA GAT TAT
   ACC CAA GGT CCA AGG TGA CCA CTG ATA GGT ATA CTA CAA GGT CTA ATA
   Trp Val Pro Gly Ser Thr Gly Asp>
   ___c_____IG K-CHAIN SP__c___C___>
                                      Tyr Pro Tyr Asp Val Pro Asp Tyr>
                                      ___d___d__HA EPITOPE___d___D___>

>NaeI
              >ApaI  >EaeI
           >Bsp1286I >BglI
              >BanII >SfiI
   >Eco0109I   >BsrFI    >BglII            >PvuII              >Bsp1286I
    >Bsp120I    >NgoMI    >BstYI   >EcoRV   >MspA1I              >BanII
        |         |         |        |         |                    |
        *  170    *  180    *  190   *  200    *
        *    *    *    *    *    *   *    *    *
   GCT GGG GCC CAG CCG GCC AGA TCT GAT ATC CAG CTG ACC CAG AGC CCA
   CGA CCC CGG GTC GGC CGG TCT AGA CTA TAG GTC GAC TGG GTC TCG GGT
   Gly Ala Gln Pro Ala Arg Ser>
   ___b___b___MISC____b___b___>
   Ala>
   ___>
                                      Asp Ile Gln Leu Thr Gln Ser Pro>
                                      ___j___j____B22 VL_j___j___j___>
```

Fig. 4A

```
                                              >HaeII
   210           220           230     |        240           250
    *             *             *               *             *
   AGC AGC CTG AGC GCC AGC GTG GGT GAC AGA GTG ACC ATC ACC TGT AAG
   TCG TCG GAC TCG CGG TCG CAC CCA CTG TCT CAC TGG TAG TGG ACA TTC
   Ser Ser Leu Ser Ala Ser Val Gly Asp Arg Val Thr Ile Thr Cys Lys>
   ___j___j___j___j___j___j____H22 VL_j___j___j___j___j___j___j___>

260           270           280           290           300
    *             *             *             *             *
   TCC AGT CAA AGT GTT TTA TAC AGT TCA AAT CAG AAG AAC TAC TTG GCC
   AGG TCA GTT TCA CAA AAT ATG TCA AGT TTA GTC TTC TTG ATG AAC CGG
   Ser Ser Gln Ser Val Leu Tyr Ser Ser Asn Gln Lys Asn Tyr Leu Ala>
   ___j___j___j___j___j___j____H22 VL_j___j___j___j___j___j___j___>

>KpnI
         |
   >BanI |
       | |
   >Acc65I
       | |
       | | 310           320           330           340           350
       *|*             *             *             *             *
   TGG TAC CAG CAG AAG CCA GGT AAG GCT CCA AAG CTG CTG ATC TAC TGG
   ACC ATG GTC GTC TTC GGT CCA TTC CGA GGT TTC GAC GAC TAG ATG ACC
   Trp Tyr Gln Gln Lys Pro Gly Lys Ala Pro Lys Leu Leu Ile Tyr Trp>
   ___j___j___j___j___j___j____H22 VL_j___j___j___j___j___j___j___>

>MspAlI
                                                     |
        360           370           380           390|          400
         *             *             *             * |           *
   GCA TCC ACT AGG GAA TCT GGT GTG CCA AGC AGA TTC AGC GGT AGC GGT
   CGT AGG TGA TCC CTT AGA CCA CAC GGT TCG TCT AAG TCG CCA TCG CCA
   Ala Ser Thr Arg Glu Ser Gly Val Pro Ser Arg Phe Ser Gly Ser Gly>
   ___j___j___j___j___j___j____H22 VL_j___j___j___j___j___j___j___>

>KpnI
         |
   >Acc65I
       | |
   >BanI| |          >BpmI
       | | |          |
       | | | 410      | 420           430           440
       *|*|*         |*             *             *             *
   AGC GGT ACC GAC TTC ACC TTC ACC ATC AGC AGC CTC CAG CCA GAG GAC
   TCG CCA TGG CTG AAG TGG AAG TGG TAG TCG TCG GAG GTC GGT CTC CTG
   Ser Gly Thr Asp Phe Thr Phe Thr Ile Ser Ser Leu Gln Pro Glu Asp>
   ___j___j___j___j___j___j____H22 VL_j___j___j___j___j___j___j___>
```

Fig. 4B

```
                                          StyI
                    >BseRI        >BssSI     >EaeI  |
   450       460    | 470      480       490  |    |
    *    *    *  *  |*    *    *    *    *    |    *
   ATC GCC ACC TAC TAC TGC CAT CAA TAC CTC TCC TCG TGG ACG TTC GGC
   TAG CGG TGG ATG ATG ACG GTA GTT ATG GAG AGG AGC ACC TGC AAG CCG
   Ile Ala Thr Tyr Tyr Cys His Gln Tyr Leu Ser Ser Trp Thr Phe Gly>
   __j___j___j___j___j___j____H22 VL_j___j___j___j___j___j___j___>

>Bsp1286I
                                  |
                              >BanII
                                  |
                              >SacI
                                  |
                              >BsiHKAI           >BsaWI
         >StyI               >Ecl136II           >BspEI
         |                        |                |
   500   |   510     520        530      540
    *    |    *  *    *    *    *    *    |    *
   CAA GGG ACC AAG GTG GAA ATC AAG AGC TCT GGC GGT GGC GGC TCC GGA
   GTT CCC TGG TTC CAC CTT TAG TTC TCG AGA CCG CCA CCG CCG AGG CCT
                                   Ser Ser Gly Gly Gly Gly Ser Gly>
                                   __a___a____LINKER_a___a___a___>
   Gln Gly Thr Lys Val Glu Ile Lys>
   ___j___j____H22 VL_j___j___j___>

>BamHI
                            |
         >MspAlI        >BstYI              >PflMI     >BsrBI
         |               |                    |          |
   550   |   560         |   570     580      |   590    |
    *    |    *    *     |    *    *    *     |    *     |
   GGT GGA GGC AGC GGA GGG GGT GGA TCC GAG GTC CAA CTG GTG GAG AGC
   CCA CCT CCG TCG CCT CCC CCA CCT AGG CTC CAG GTT GAC CAC CTC TCG
   Gly Gly Gly Ser Gly Gly Gly Gly Ser>
   __a___a___a_LINKER____a___a___a___>
                                     Glu Val Gln Leu Val Glu Ser>
                                     __e___e_H22 VH___e___e___>

>BsrFI
                          |
                    >EaeI          >BseRI
                      |              |
   600       610    | 620         |630        640
    *    *    *  *  |*    *    *  |  *    *    *
   GGT GGA GGT GTT GTG CAA CCT GGC CGG TCC CTG CGC CTG TCC TGC TCC
   CCA CCT CCA CAA CAC GTT GGA CCG GCC AGG GAC GCG GAC AGG ACG AGG
   Gly Gly Gly Val Val Gln Pro Gly Arg Ser Leu Arg Leu Ser Cys Ser>
   __e___e___e___e___e___e____H22 VH_e___e___e___e___e___e___e___>
```

Fig. 4C

```
                                          >AflIII                              >BanI
              650         660         670         680
               *           *           *|*          *           *
        TCG TCT GGC TTC ATT TTC AGT GAC AAT TAC ATG TAT TGG GTG AGA CAG
        AGC AGA CCG AAG TAA AAG TCA CTG TTA ATG TAC ATA ACC CAC TCT GTC
        Ser Ser Gly Phe Ile Phe Ser Asp Asn Tyr Met Tyr Trp Val Arg Gln>
        ___e___e___e___e___e___e___H22 vh_e___e___e___e___e___e___e___>

>EcoNI
       690    |    700         710         720         730
        *     |*    *           *           *           *           *
        GCA CCT GGA AAA GGT CTT GAG TGG GTT GCA ACC ATT AGT GAT GGT GGT
        CGT GGA CCT TTT CCA GAA CTC ACC CAA CGT TGG TAA TCA CTA CCA CCA
        Ala Pro Gly Lys Gly Leu Glu Trp Val ala Thr Ile Ser Asp Gly Gly>
        ___e___e___e___e___e___e___H22 VH_e___e___e___e___e___e___e___>

740         750         760         770         780
             *           *           *           *           *
        AGT TAC ACC TAC TAT CCA GAC AGT GTG AAG GGA AGA TTT ACA ATA TCG
        TCA ATG TGG ATG ATA GGT CTG TCA CAC TTC CCT TCT AAA TGT TAT AGC
        Ser Tyr Thr Tyr Tyr Pro Asp Ser Val Lys Gly Arg Phe Thr Ile Ser>
        ___e___e___e___e___e___E___H22 VH_e___e___e___e___e___e___e___>

>BsaI
            790         800         810         820    |    830
             *           *           *           *     |*    *
        AGA GAC AAC AGC AAG AAC ACA TTG TTC CTG CAA ATG GAC AGC CTG AGA
        TCT CTG TTG TCG TTC TTG TGT AAC AAG GAC GTT TAC CTG TCG GAC TCT
        Arg Asp Asn Ser Lys Asn Thr Leu Phe Leu Gln Met Asp Ser Leu Arg>
        ___e___e___e___e___e___e___H22 VH_e___e___e___e___e___e___e___>

>DrdI
            >BbsI                                    >SfcI
            840  |     850         860         870|        880
             *   |      *           *           *|         *
        CCC GAA GAC ACC GGG GTC TAT TTT TGT GCA AGA GGC TAC TAT AGG TAC
        GGG CTT CTG TGG CCC CAG ATA AAA ACA CGT TCT CCG ATG ATA TCC ATG
        Pro Glu Asp Thr Gly Val Tyr Phe Cys Ala Arg Gly Tyr Tyr Arg Tyr>
        ___e___e___e___e___e___e___H22 VH_e___e___e___e___e___e___e___>

>BseRI
                                            >PpuMI  >BstEII
                                  >StyI  > Eco0109I                  >BsmBI
            890         900         910         920
             *           *           *|*          *           *
        GAG GGG GCT ATG GAC TAC TGG GGC CAA GGG ACC CCG GTC ACC GTC TCC
        CTC CCC CGA TAC CTG ATG ACC CCG GTT CCC TGG GGC CAG TGG CAG AGG
        Glu Gly Ala Met Asp Tyr Trp Gly Gln Gly Thr Pro Val Thr Val Ser>
        ___e___e___e___e___e___e___H22 VH_e___e___e___e___e___e___e___>
```

Fig. 4D

```
                                    >HincII
                           >PstI     |
                            |
    >MspAlI    >SfcI       >AccI
     |          |           |
>BspMI  |>SacII |   >SalI           >EarI           >BstYI
 |      |  |    |   | |              |                |
 930    |  | 940|   | |    950       |   960          |  970
  |     *  *  | *   * *     |        *    |           *   |
  *          |    *     *     *   *    *      *    *    *     *
  TCA CCG CGG CTG CAG GTC GAC GAA CAA AAA CTC ATC TCA GAA GAG GAT
  AGT GGC GCC GAC GTC CAG CTG CTT GTT TTT GAG TAG AGT CTT CTC CTA
  Ser>
  ___>
       Pro Arg Leu Gln Val Asp>
       __f___f_MISC__f___f___>
                                Glu Gln Lys Leu Ile Ser Glu Glu Asp>
                                __h___h___MYC EPITOPE_h___h___h___>

>BanI
                                                  |
              >BamI                         >MslI |
               |                             |    |
  980          |   990           1000       1010  |        1020
   *           *    *     *       *    *     |*    *   *     *
   *           *    *     *       *    *     *    *    *     *
  CTG AAT GCT GTC GGC CAG GAC ACG CAG GAG GTC ATC GTG GTG CCA CAC
  GAC TTA CGA CAC CCG GTC CTG TGC GTC CTC CAG TAG CAC CAC GGT GTG
      Asn>
      ___>
  Leu>
  ___>
           Ala Val gly Gln Asp Thr Gln Glu Val Ile Val Val Pro His>
           __i___i___i___i__PDGFR TM DOMAIN_i___i___i___i___i___>

>XcmI
                                                     |
                                               >BglI |
                                                |    |
     1030         1040          1050         1060    |      1070
      *    *       *    *        *    *        |*     *    *
      *    *       *    *        *    *        *     *     *
  TCC TTG CCC TTT AAG GTG GTG GTG ATC TCA GCC ATC CTG GCC CTG GTG
  AGG AAC GGG AAA TTC CAC CAC CAC TAG AGT CGG TAG GAC CGG GAC CAC
  Ser Leu Pro Phe Lys Val Val Val Ile Ser Ala Ile Leu Ala Leu Val>
  __i___i___i___i___i__PDGFR TM DOMAIN_i___i___i___i___i___i___>

>BsiHKAI
     |
  >Bsp1286I
     |
     | 1080        1090          1100         1110         1120
     *    *        *     *        *    *        *    *       *
     *    *        *     *        *    *        *    *       *
  GTG CTC ACC ATC ATC TCC CTT ATC ATC CTC ATC ATG CTT TGG CAG AAG
  CAC GAG TGG TAG TAG AGG GAA TAG TAG GAG TAG TAC GAA ACC GTC TTC
  Val Leu Thr Ile Ile Ser Leu Ile Ile Leu Ile Met Leu Trp Gln Lys>
  __i___i___i___i___i__PDGFR TM DOMAIN_i___i___i___i___i___i___>

1130
            *    *
  AAG CCA CGT T AG
  TTC GGT GCA A TC
  Lys Pro Arg>                  Fig. 4E
  __i___i___>
```

Sequence Range: 1 to 1135

```
                                    >BamHI
                                      |
                                    >BstYI
                                      |
                                    BanII
                                      |
                                    >SacI
                                      |
              >KpnI      >Bsp1286I           >BsiEI              >ApoI
              |         |                     |                  |
      >BanI   |>Ecl136II     >SpeI    >EaeI              >EcoRI
      |       ||            |         |                   |
>HindIII >Acc65I  >BsiHKAI        >EagI           >BstXI
  |     |  |     |            |         |             |  |
  |     |  | 10  |   20           30         40           50            60
  |     |  |  *  |    *            *          *            *             *
  AAGCTTGGTA CCGAGCTCGG ATCCACTAGT AACGGCCGCC AGTGTGCTGG AATTCGGCTT
  TTCGAACCAT GGCTCGAGCC TAGGTGATCA TTGCCGGCGG TCACACGACC TTAAGCCGAA >NcoI
                |
    >EcoRV  >StyI
      |      |
      |   70 |         80         90         100        110
      |    * |          *          *          *          *
  GGGGATATCC ACC ATG GAG ACA GAC ACA CTC CTG CTA TGG GTA CTG CTG CTC
  CCCCTATAGG TGG TAC CTC TGT CTG TGT GAG GAC GAT ACC CAT GAC GAC GAG
             Met Glu Thr Asp Thr Leu Leu Leu Trp Val Leu Leu Leu
             __b__b__b__b_IG K_CHAIN SP___b___b___b___b___>

>NdeI
                                            |
        120        130        140           150        160
         *          *          *    |        *          *
  TGG GTT CCA GGT TCC ACT GGT GAC TAT CCA TAT GAT GTT CCA GAT TAT
  ACC CAA GGT CCA AGG TGA CCA CTG ATA GGT ATA CTA CAA GGT CTA ATA
  Trp Val Pro Gly Ser Thr Gly Asp>
  __b___IG K-CHAIN SP__b___b___>
                                    Tyr Pro Tyr Asp Val Pro Asp Tyr>
                                    __c___c__HA EPITOPE___c___c___>

EaeI
                        |
          >BanII    >NaeI
          |          |
      >Bsp1286I   >SfiI
      |           ||
        >ApaI    >BglI                    >SfcI
        |        ||                        |
  >Eco109I  >BsrFI    >BglII      >MspAlI  >PstI
  |         |        |            |        |
  >Bsp120I  >NgoMI  >BstYI  >BstYI   >PvuII
  |         |       |       |        |
  |      170|      180     190       |200
  |       * |       *       *        |  *
  GCT GGG GCC CAG CCG GCC AGA TCT GAG ATC CAG CTG CAG CAG ACT GGA
  CGA CCC CGG GTC GGC CGG TCT AGA CTC TAG GTC GAC GTC GTC TGA CCT
  Ala>
  __>
                                  Glu Ile Gln Leu Gln Gln Thr Gly>
                                  ___f___f____A77 VH_f___f___f___>
  Gly Ala Gln Pro Ala Arg Ser>
  ___j___j__MISC___j___j___>
```

Fig. 10A

```
                  >Eco57I                                      >EcoRV
     210         |220         230         240    |    250
      *     *     |*     *     *     *     *    |*     *     *
     CCT GAG CTG GTG AAG CCT GGG GCT TCA GTG AAG ATA TCC TGC AAG GCT
     GGA CTC GAC CAC TTC GGA CCC CGA AGT CAC TTC TAT AGG ACG TTC CGA
     Pro Glu Leu Val Lys Pro Gly Ala Ser Val Lys Ile Ser Cys Lys Ala>
     __f___f___f___f___f___f___A77 VH_f___f___f___f___f___f___f___>

>NcoI
                                                              >StyI
     260         270         280         290         300       |
      *     *     *     *     *     *     *     *     *     *  |
     TCT GGT TAT TCA TTC ACT GAC TAC ATC ATA TTT TGG GTG AAG CAG AGC
     AGA CCA ATA AGT AAG TGA CTG ATG TAG TAT AAA ACC CAC TTC GTC TCG
     Ser Gly Tyr Ser Phe Thr Asp Tyr Ile Ile Phe Trp Val Lys Gln Ser>
     __f___f___f___f___f___f___A77 VH_f___f___f___f___f___f___f___>

>AseI
                                       >SspI
     310         320         330         |340         350
      *     *     *     *     *     *   |*     *     *     *
     CAT GGA AAG AGC CTT GAG TGG ACT GGA AAT ATT AAT CCT TAC TAT GGT
     GTA CCT TTC TCG GAA CTC ACC TGA CCT TTA TAA TTA GGA ATG ATA CCA
     His Gly Lys Ser Leu Glu Trp Thr Gly Asn Ile Asn Pro Tyr Tyr Gly>
     __f___f___f___f___f___f___A77 VH_f___f___f___f___f___f___f___>

>AccI
     >ScaI                                 >Eco57I    >SfcI   |
     |                                     |          |       |
     |   360         370         380       |390       |400
     |    *     *     *     *     *     *  |*   *     |*    *|*
     AGT ACT AGC TAC AAT CTG AAG TTC AAG GGC AAG GCC ACA TTG ACT GTA
     TCA TGA TCG ATG TTA GAC TTC AAG TTC CCG TTC CGG TGT AAC TGA CAT
     Ser Thr Ser Tyr Asn Leu Lys Phe Lys Gly Lys Ala Thr Leu Thr Val>
     __f___f___f___f___f___f___A77 VH_f___f___f___f___f___f___f___>

410         420         430         440
           *     *     *     *     *     *     *     *
          GAC AAA TCT TCC AGC ACA GCC TAC ATG CAG CTC AAC AGT CTG ACA TCT
          CTG TTT AGA AGG TCG TGT CGG ATG TAC GTC GAG TTG TCA GAC TGT AGA
          Asp Lys Ser Ser Ser Thr Ala Tyr Met Gln Leu Asn Ser Leu Thr Ser>
          __f___f___f___f___f___f___A77 VH_f___f___f___f___f___f___f___>

PstI
                      >DrdI
                  >SfcI|   |                                  >BseRI
     450         |460 |   |470         480         490        |
      *     *   |*|    |*|*    *     *     *     *     *    |*
     GAG GAC TCT GCA GTC TAT TAC TGT GTA AGA GGA GTT TAT TAC TAC GGT
     CTC CTG AGA CGT CAG ATA ATG ACA CAT TCT CCT CAA ATA ATG ATG CCA
     Glu Asp Ser Ala Val Tyr Tyr Cys Val Arg Gly Val Tyr Tyr Tyr Gly>
     __f___f___f___f___f___f___A77 VH_f___f___f___f___f___f___f___>
```

Fig. 10B

```
                                              >StyI
                                                |
        500         510         520         530         540
         *           *           *           *           *
    AGT AGC TAC GAG GCG TTT CCT TAC TGG GGC CAA GGG ACT CTG GTC ACT
    TCA TCG ATG CTC CGC AAA GGA ATG ACC CCG GTT CCC TGA GAC CAG TGA
    Ser Ser Tyr Glu Ala Phe Pro Tyr Trp Gly Gln Gly Thr Leu Val Thr>
    ___f___f___f___f___f___f____A77 VH_f___f___f___f___f___f___f___>

>PstI          >BsaWI                    >BseRI
                |              |                         |
       >SfcI    |      >BspEI  |                 >MspAlI |
         |      |        |     |                    |    |
        550         560         570         580         590
         *           *           *           *           *
    GTC TCT GCA GGA GGT GGC GGC TCC GGA GGA GGT GGC AGC GGA GGG GGC
    CAG AGA CGT CCT CCA CCG CCG AGG CCT CCT CCA CCG TCG CCT CCC CCG
                Gly Gly Gly Gly Ser Gly Gly Gly Gly Ser Gly Gly Gly>
                ___a___a___a___a___a_LINKER_a___a___a___a___a___>
    Val Ser Ala>
    ___f___f___>

>BamHI
     |
  >BstYI
     |   600         610         620         630         640
     |    *           *           *           *           *
    GGA TCC GAT GTT GTG ATG ACC CAG ACT CCA CTC ACT TTG TCG ATT ACC
    CCT AGG CTA CAA CAC TAC TGG GTC TGA GGT GAG TGA AAC AGC TAA TGG
    Gly Ser>
    ___a___>
            Asp Val Val Met Thr Gln Thr Pro Leu Thr Leu Ser Ile Thr>
            ___g___g___g___g___g____A77 VK_g___g___g___g___g___g___>

650         660         670         680
         *           *           *           *
    ATT GGA CAA CCA GCC TCC ATC TCT TGC AAG TCA AGT CAG AGC CTC TTA
    TAA CCT GTT GGT CGG AGG TAG AGA ACG TTC AGT TCA GTC TCG GAG AAT
    Ile Gly Gln Pro Ala Ser Ile Ser Cys Lys Ser Ser Gln Ser Leu Leu>
    ___g___g___g___g___g___g____A77 VK_g___g___g___g___g___g___g___>

690         700         710         720         730
     *           *           *           *           *
    GAT AGT GAT GGA AAG ACA TAT TTG AAT TGG TTG TTA CAG AGG CCA GGC
    CTA TCA CTA CCT TTC TGT ATA AAC TTA ACC AAC AAT GTC TCC GGT CCG
    Asp Ser Asp Gly Lys Thr Tyr Leu Asn Trp Leu Leu Gln Arg Pro Gly>
    ___g___g___g___g___g___G____A77 VK_g___g___g___g___g___g___g___>

>DrdI
                                                              |
        740         750         760         770         780
         *           *           *           *           *
    CAG TCT CCA ACG CGC CTA ATC TAT CTG GTG TCT AAA CTG GAC TCT GGA
    GTC AGA GGT TGC GCG GAT TAG ATA GAC CAC AGA TTT GAC CTG AGA CCT
    Gln Ser Pro Thr Arg Leu Ile Tyr Leu Val Ser Lys Leu Asp Ser Gly>
    ___g___g___g___g___g___g____A77 VK_g___g___g___g___g___g___g___>
```

Fig. 10C

```
                                      >BpmI
            790          800  |       810          820          830
             *            *   |        *            *            *
         GTC CCT GAC AGG TTC ACT GGC AGT GGA TCA GGG ACA GAT TTC ACA CTG
         CAG GGA CTG TCC AAG TGA CCG TCA CCT AGT CCC TGT CTA AAG TGT GAC
         Val Pro Asp Arg Phe Thr Gly Ser Gly Ser Gly Thr Asp Phe Thr Leu>
         ___g___g___g___g___g___g___A77_VK_g___g___g___g___g___g___g___>

>ApoI
            840          850          860    |     870          880
             *            *            *     |      *            *
         AAA ATC AGC AGA GTG GAG GCT GAG GAT TTG GAA TTT TAT TAT TGC TGG
         TTT TAG TCG TCT CAC CTC CGA CTC CTA AAC CTT AAA ATA ATA ACG ACC
         Lys Ile Ser Arg Val Glu Ala Glu Asp Leu Gly Ile Tyr Tyr Cys Trp>
         ___g___g___g___g___g___g___A77_VK_g___g___g___g___g___g___g___>

>Bsp1286I
              >BsiHKAI
    >ApaLI    |                                >BanI
       |      |890          900          910  |   920
       |       *            *            *    |    *            *
         CAA GGT GCA CAT TTT CCT CAG ACG TTC GGT GGA GGC ACC AAG CTG GAA
         GTT CCA CGT GTA AAA GGA GTC TGC AAG CCA CCT CCG TGG TTC GAC CTT
         Gln Gly Ala His Phe Pro Gln Thr Phe Gly Gly Gly Thr Lys Leu Glu>
         ___g___g___g___g___g___g___A77_VK_g___g___g___g___g___g___g___>

>HincII
                             >PstI  |
                              |     |
          >MspA1I   >SfcI  |>AccI
             |      |     |>SalI
          >BspMI |>SacII  |||                    >EarI        >BstYI
         930  |  |940     |||  950          960    |    970     |
             *            *            *            *            *
         ATC AAA CCG CGG CTG CAG GTC GAC GAA CAA AAA CTC ATC TCA GAA GAG
         TAG TTT GGC GCC GAC GTC CAG CTG CTT GTT TTT GAG TAG AGT CTT CTC
                                         Glu Gln Lys Leu Ile Ser Glu Glu>
                                         ___d___d_MYC_EPITOPE___d___d___>
         Ile Lys>
         ___g___>
                    Pro Arg Leu Gln Val Asp>
                    ___h___h_MISC__h___h___>

>BanI
                                                                |
                     >BsmI                           >MslI
            980      |   990          1000         1010|      1020
             *       |    *            *            *  ||      *
         GAT CTG AAT GCT GTG GGC CAG GAC ACG CAG GAG GTC ATC GTG GTG CCA
         CTA GAC TTA CGA CAC CCG GTC CTG TGC GTC CTC CAG TAG CAC CAC GGT
         Asp Leu>
         ___d___>
                    Ala Val Gly Gln Asp Thr Gln Glu Val Ile Val Val Pro>
                    ___e___e___e___e_PDGFR_TM_DOMAIN___e___e___e___e___>   Fig. 10D
                 Asn>
                 ___>
```

```
                                                              >XcmI
                                                             >BglI
      1030          1040          1050          1060    |  |  1070
   *     *     *     *     *     *     *     *     *   |  |  *     *
   CAC TCC TTG CCC TTT AAG GTG GTG GTG ATC TCA GCC ATC CTG GCC CTG
   GTG AGG AAC GGG AAA TTC CAC CAC CAC TAG AGT CGG TAG GAC CGG GAC
   His Ser Leu Pro Phe lys Val Val Val Ile Ser Ala Ile Leu Ala Leu>
   ___e___e___e___e___e___PDGFR TM DOMAIN_e___e___e___e___e___e___>

>BsiHKAI
   >Bsp1286I
      1080          1090          1100          1110          1120
   *     *     *     *     *     *     *     *     *     *     *
   GTG GTG CTC ACC ATC ATC TCC CTT ATC ATC CTC ATC ATG CTT TGG CAG
   CAC CAC GAG TGG TAG TAG AGG GAA TAG TAG GAG TAG TAC GAA ACC GTC
   Val Val Leu Thr Ile Ile Ser Leu Ile Ile Leu Ile Met Leu Trp Gln>
   ___e___e___e___e___e___PDGFR TM DOMAIN_e___e___e___e___e___e___>

1130
   *     *     *
   AAG AAG CCA CGT TAG
   TTC TTC GGT GCA ATC
   Lys Lys Pro Arg>
   ___PDGFR TM_____>
```

Fig. 10E

CELLS EXPRESSING ANTI-FC RECEPTOR BINDING COMPONENTS

RELATED APPLICATIONS

This application claims priority to U.S. Ser. No. 60/067,232, filed on Dec. 2, 1997, the contents of which are incorporated herein by reference.

BACKGROUND OF THE INVENTION

Antigen-specific antibodies increase the uptake of antigen, resulting in enhanced T cell activation (Chang, T. W., *Immunol. Today*, 6:245, 1985). Antibody:antigen immune complexes bind to Fc receptors present on the surface of antigen presenting cells (APC), such as macrophages. These complexes are then internalized and the antigen is processed and presented in the context of MHC-encoded molecules to antigen-specific T cells. Thus, the presence of antigen-specific antibodies can reduce the level of antigen required to activate T cells (Gosselin, E. J., et al., *J. Immunol.*, 149:3477, 1992).

Receptors for the Fc portion of IgG (FcγR) have been characterized at the molecular level. Human monocytes and macrophages express three major classes of FcγR, identified as FcγRI, FcγRII, and FcγRIII. Targeting tetanus toxoid to either FcγRI or FcγRII on monocytes reduces the concentration of antigen required to stimulate T cell proliferation in vitro by a factor of 100–1000 (Kovacsovics-Bakowski, M., et al., *Proc. Natl. Acad. Sci. USA*, 90:4942, 1993). Therefore, targeting antigen to specific FcγR on APC can dramatically decrease the amount of antigen required to stimulate a specific T cell response.

Following phagocytosis by a monocyte or a macrophage, antigens can be processed and presented to cytolytic T lymphocytes (CTL; Falo, L. D., et al., *Nat. Med.* 1:649, 1995). It has been shown that mice immunized with an iron particle coupled to a tumor antigen are protected from tumors expressing that tumor antigen (Kovacsovic-Bankowski, M., et al., ibid). Therefore, by inducing monocytes or macrophages to phagocytose tumor antigens, protective immunity to tumors can be induced.

SUMMARY OF THE INVENTION

The present invention provides a cell which is transformed to express on its surface a component which binds to an Fc receptor of an effector cell. In particular embodiments, the Fc receptor binding component on the cell is an antibody or portion thereof, such as a single chain Fv fragment, which binds to the Fcα receptor or the Fcγ receptor present on effector cells. The transformed cell is thus targeted to the effector cell via the Fc binding component, and can be used as a vehicle to increase an effector cell-mediated immune response, such as cell lysis and phagocytosis, against an antigen associated with the cell. Examples of target antigens include, but are not limited to tumor antigens, such as HER-2 neu, TAG 72, carcinoembryonic antigen and gastrin releasing peptide receptor, and components from pathogens, such as a virus, fungus, protozoan, or bacterium.

The anti-Fc receptor binding component is produced recombinantly within the target cell in a manner which causes it to be expressed on the surface of the cell. In a preferred embodiment, the anti-Fc receptor binding component is able to bind an Fc receptor of an effector cell without being blocked by endogenous antibody, e.g., IgG or IgA. In another preferred embodiment, the anti-Fc receptor binding component is an antibody or antibody fragment, such as an IgA, IgG, IgM, IgE, or fragment thereof (e.g., Fab, Fab', F(ab')$_2$, Fv, or single chain Fv fragment).

In a particular embodiment of the invention, the anti-Fc receptor binding component is expressed recombinantly as a fusion protein associated with the membrane of the target (transformed) cell. For example, the anti-Fc receptor binding component can be expressed in the cell as a fusion protein together with a transmembrane protein or portion thereof (e.g., transmembrane domain of the protein). In such embodiments, a preferred anti-Fc receptor binding component comprises an anti-Fc receptor antibody or antibody fragment, such as humanized anti-FcγR antibody 22 (H22) having the ATCC deposit number CRL 11177, anti-FcαR monoclonal antibody A77 (Monteiro et al. (1992) *J. Immunol.* 148:1764).or a single chain Fv fragment of H22 or A77. In a particularly preferred embodiment, the anti-Fc receptor binding component is expressed as a fusion protein made up of a single chain Fv fragment of H22 or A77 and a transmembrane protein (e.g., the transmembrane domain of the platelet derived growth factor receptor).

Accordingly, in addition to cells that express Fc receptor binding components, the present invention also provides vectors and expression plasmids, such as anti-FcγR pJG717 (SEQ ID NO:1) and anti-FcαR pJG718 (SEQ ID NO:3), which can be used to transform cells so that they express components which bind Fc receptors.

The present invention further provides a method of increasing an immune response in a subject using transformed cells of the invention. The method involves contacting the transformed cell with an effector cell in the presence of a lymphocyte, (e.g., a T cell or B cell). In one embodiment, the effector cell is treated with an agent that increases expression of Fc receptors on the surface of the effector cell. Suitable agents include cytokines, such as granulocyte-colony stimulating factor (G-CSF), granulocyte-macrophage-colony stimulating factor (GM-CSF), γ-interferon (IFN-γ), tissue necrosis factor (TNF), and combinations thereof.

Cells of the present invention can be transformed to express Fc receptor binding components either in vivo or ex vivo. In a preferred embodiment, the cell is transformed ex vivo and is then administered to a subject in vivo. Following administration, the cell binds to an effector cell via an Fc receptor of the effector cell (e.g., Fcγ receptor, an Fcα receptor, an Fc μ receptor, or Fcε receptor). In particular embodiments, the Fc receptor is an Fcγ receptor selected from FcγRI, FcγRII, and FcγRIII. Alternatively, effector cells can be taken from the subject by, for example, apherisis, modified with cytokines to optimize antigen presentation and Fc receptor functions ex vivo, combined with cells of the present invention transformed to express Fc receptor binding components, and then returned to the subject.

Among various other uses, transformed cells of the present invention can be used to induce a specific immune response against an antigen associated with the transformed cell, such as a T lymphocyte mediated immune reponse. Accordingly, transformed cells of the invention can be used to achieve protective immunity against selected antigens, e.g., as vaccines. When targeting tumor cells, for example, the present invention provides the distinct advantage in that no particular tumor antigen need be known or selected for targeting. This is because the entire tumor cell itself is transformed to express a component which binds to an effector cell via an Fc receptor to cause killing of the tumor cell. This is of great benefit since many tumors do not have defined antigens for targeting.

BRIEF DESCRIPTION OF THE DRAWINGS

FIG. 4 shows the nucleotide sequence (SEQ ID NO:1) of pJG717 and the corresponding amino acid sequence (SEQ ID NO:2) of the H22-TM coding region within the plasmid. Also shown are restriction sites, as indicated on the pJG717 map shown in FIG. 1.

FIG. 10 shows the nucleotide sequence of pJG718 and the corresponding amino acid sequence of the A77-TM coding region within the plasmid. Also shown are restriction sites, as indicated on the pJG718 map shown in FIG. 9.

DETAILED DESCRIPTION OF THE INVENTION

Figure 1:
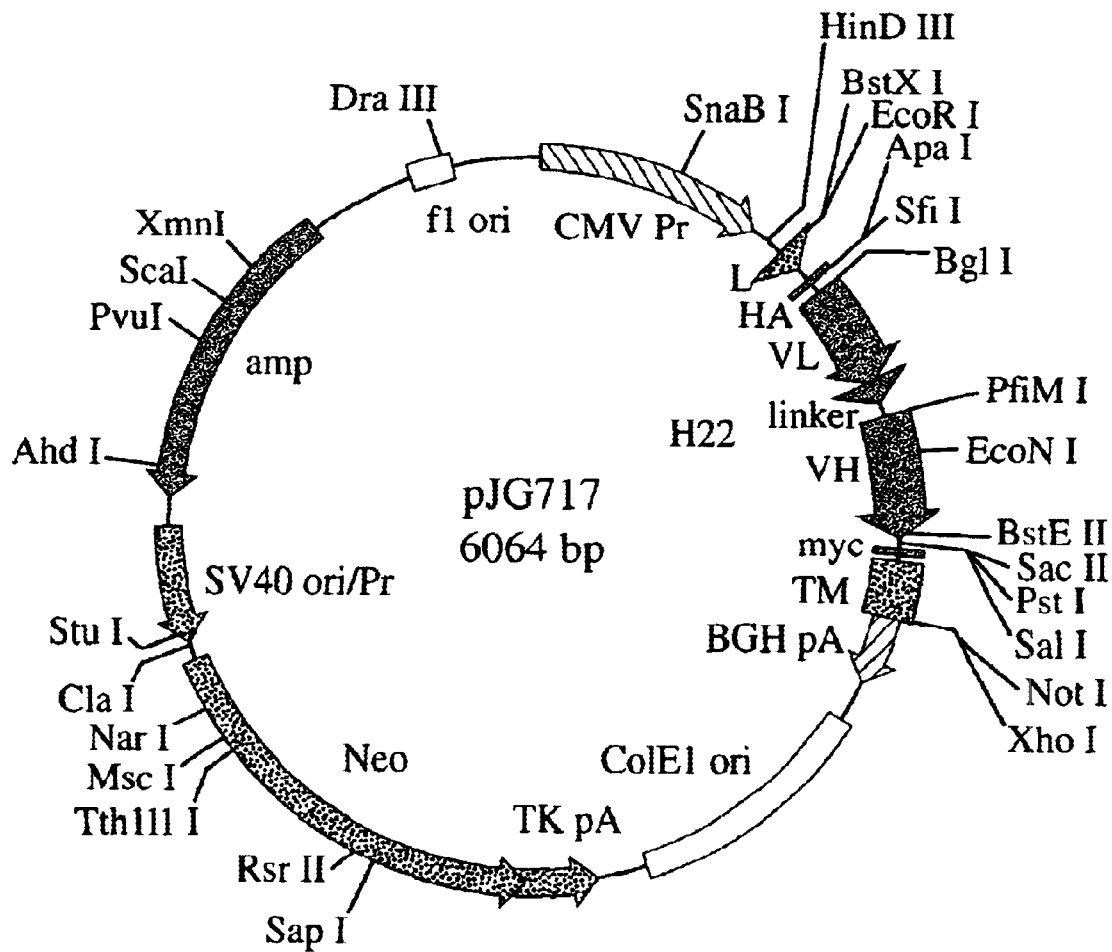
FIG. 1 is a map of the expression vector pJG717 encoding a fusion protein made up of the platelet derived growth factor receptor transmembrane domain (TM) and a single chain Fv fragment of anti-FcγRI antibody H22. This fusion protein is referred to as H22-TM. As shown on the map, CMV Pr is the CMV promoter/enhancer; L is the Murine Ig kappa-chain V-J2-C leader sequence; HA is the hemagglutinin A epitope; myc is the myc epitope; TM is the platelet derived growth factor receptor transmembrane domain; BGH pA is the bovine growth hormone polyadenylation signal; Co1E1 ori is the Co1E1 origin of replication; Tk pA is the thymidine kinase polyadenylation site; Neo is the neomycin/kanamycin resistance gene; SV40 ori/Pr is the SV40 origin and promoter; amp is the ampicillin resistance gene; and f1 ori is the f1 origin.

The present invention is described herein using the following terms and phrases which shall be understood to have the meanings provided below.

The term "subject" means any mammal (e.g., human or non-human) possessing leukocytes capable of responding to antigenic stimulation. A "patient" means a human subject.

The term "leukocyte" refers generally to a white blood cell and includes all classes of white blood cells. Leukocytes include cells from three lines of development: myeloid, lymphoid, and monocytic cells. A "lymphocyte" is a white blood cell formed in lymphatic tissue (lymph nodes, spleen, thymus, tonsils, Peyer's patches and sometimes in bone marrow, and includes B lymphocytes and T lymphocytes. A B lymphocyte is responsible for the production of immunoglobulins and expresses immunoglobulins on its surface. A T lymphocyte is responsible for cell-mediated immunity and can be further divided according to function, such as helper, suppressor, and cytotoxic T cell.

The phrase "component which binds to an Fc receptor" includes any agent capable of binding to an Fc receptor on an effector cell, such as a protein or protein fragment that binds specifically to an Fc receptor determinant. The component can be an antibody or antibody fragment as defined herein, and includes an engineered antibody such as a humanized or a chimeric antibody, a Fab fragment consisting of the $V_L$, $V_H$, $C_L$ and $C_{H1}$ domains; an Fd fragment consisting of the $V_H$ and $C_{H1}$ domains; an Fv fragment consisting of the $V_L$ and $V_H$ domains of a single arm of an antibody; a dAb fragment (Ward et al., 1989 *Nature* 341:544–546) consisting of a $V_H$ domain; an isolated complementarity determining region (CDR); and an F(ab')$_2$ fragment, a bivalent fragment comprising two Fab' fragments linked by a disulfide bridge at the hinge region. The component can also be a peptide mimetic which mimics the binding of an antibody or antibody fragment as defined herein. The component can also be a chemical compound, such as a cyanidin reagent, which binds to an Fc receptor.

The component which binds to an Fc receptor can also be an engineered binding protein specifically selected for binding to the Fc, and can be obtained by selection from a variegated protein display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370–1372; Hay et al. (1992) Hum Antibod Hybridomas 3:81–85; Huse et al. (1989) Science 246:1275–1281; Griffths et al. (1993) EMBO J. 12:725–734; Hawkins et al. (1992) J. Mol Biol 226:889–896; Clackson et al. (1991) Nature 352:624–628; Gram et al. (1992) PNAS 89:3576–3580; Garrad et al. (1991) Bio/Technology 9:1373–1377; Hoogenboom et al. (1991) Nuc Acid Res 19:4133–4137; and Barbas et al. (1991) PNAS 88:7978–7982.

The component which binds to an Fc receptor can also be a non-immunoglobulin ligand.

The term "infectious disease" means a disorder caused by one or more species of bacteria, viruses, fungi, or protozoans, referred to as "pathogens." In this invention, pathogens are exemplified, but not limited to, *Mycobacterium tuberculosis, M. leprae, Pseudomonas aeruginosa, Shigella dysenteria, Salmonella typhi, S. paratyphi, Staphylococcus aureus, Streptococcus hemolyticus, Hemophilus pneumoniae, Escherichia coli* serotype 0157, Chlamydia species, Helicobacter species; human immunodeficiency viruses HIV-1, -2, and -3, human herpes virus (HSV-I and -II), non-A non-B non-C hepatitis virus, human papilloma virus (HPV), cytomegalovirus (CMV), human T-cell leukemia virus (HTLV-I and II), feline leukemia virus (FeLV), simian immune deficiency virus (SIV), and rous sarcoma virus (RSV), pox viruses, rabies viruses; Aspergillus species; *Entamoeba histolytica,* Giardia species; and Newcastle disease virus.

The terms "protein," "polypeptide" and "peptide" are used interchangeably herein.

The term "substantially pure" with respect to a population of genetically modified cells means that the cells contain fewer than about 20%, more preferably fewer than about 10%, most preferably fewer than about 5%, non-modified cells.

The term "substantially pure" with respect to a nucleic acid or a protein means that the nucleic acid or protein is at least about 75%, preferably at least about 85%, more preferably at least about 90%, and most preferably at least about 95% free of other nucleic acids or proteins.

The term "culture medium" refers generally to any preparation suitable for cultivating living cells. A "cell culture" refers to a cell population sustained in vitro.

A "transgenic animal" means an animal, preferably a non-human animal having one or more cells containing a heterologous nucleic acid. The nucleic acid is introduced into the one or more cells by genetic manipulation. The term "genetic manipulation" means the introduction of a recombinant DNA molecule into a cell. Typical transgenic animals of the invention express a recombinant form of a gene encoding an Fc receptor ("FcR"), such as a human FcR. A "transgenic animal" also includes an animal having an endogenous gene which is disrupted by genetic manipulation, such as a gene encoding a murine FcR.

The term "fusion protein" means a non-naturally occurring protein obtained from genetic manipulation of two or more genes encoding respectively two or more different proteins in the same translational reading frame (i.e., genetically linked). Translation of the fusion gene produces a fusion protein, which has elements of each of the two or more different proteins that contributed to it. Fusion proteins of the present invention comprise at least a component which binds to an Fc receptor and a transmembrane protein.

The term "transmembrane protein" refers to a protein that comprises a portion that spans a biological membrane, such as a cell membrane, a nuclear membrane, or a mitochondrial membrane. The transmembrane protein portion found within the membrane is the "transmembrane domain" or "transmembrane region" and is enriched in hydrophobic amino acid residues such as tryptophan, tyrosine, phenylalanine, leucine, isoleucine and valine, in comparison to, for example, extracellular or cytoplasmic domains of the protein.

The term "transgene" means a nucleic acid sequence (encoding, e.g., an FcR protein), which is partly or entirely heterologous, i.e., foreign, to the transgenic animal or cell into which it is introduced, or, is homologous to an endogenous gene of the transgenic animal or cell into which it is introduced, but which is designed to be inserted into the animal's genome in such a way as to alter the genome of the cell into which it is inserted (e.g., it is inserted at a location which differs from that of the natural gene or its insertion results in "a knockout"). A transgene can include one or more transcriptional regulatory sequences and any other nucleic acid, such as introns, that may be necessary for optimal expression of a selected nucleic acid.

The term "vector" refers to a nucleic acid molecule capable of transporting another nucleic acid to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

The terms "transformation" and "transfection" mean the introduction of a nucleic acid, e.g., an expression vector, into a recipient cell.

The term "gene product" includes an RNA molecule transcribed from a gene, or a protein translated from the gene.

Introduction

The present invention is based on the discovery that selected cells can be targeted for killing by genetically modifying the target cell (e.g. a tumor cell or a cell infected with a pathogen) to express on its surface a component which binds to an Fc receptor on an effector cell. The target cell then binds to an effector cell which processes and presents antigens associated with the target cell to immune cells, such as T and B lymphocytes, causing a cascade of immune events which result in killing (e.g., via ADCC or phagocytosis) of the target cell. Thus, the invention allows for killing of target cells without targeting any particular antigen on the cell. This provides a great advantage since many tumor cells and other target cells do not have defined (e.g., known) antigens for targeting.

In particular embodiments, the invention provides an expression vector which can be used to genetically modify (i.e., transform) a target cell to express one or more Fe receptor binding components on its surface. In another embodiments, the invention provides a target cell transformed with the aforementioned expression vector. In still other embodiments, the invention provides methods of using the expression vectors and transformed cells to effect or enhance a target cell-specific or antigen-specific immune response (e.g., to obtain a protective immune response against a particular antigen).

Expression Vectors for Genetically Modifying Target Cells

Expression vectors for use in the invention encode an anti-Fc receptor binding protein which, once expressed, is presented on the surface of a selected target cell. In all cases, the anti-Fc receptor binding protein must be sufficiently exposed on the cell surface to enable it to bind to an Fc receptor exterior to the cell.

In one embodiment, this is achieved by co-expression of the anti-Fc receptor binding component with a protein which naturally associates with (e.g., inserts into) the cell membrane (i.e., a transmembrane (TM) protein). Accordingly, expression vectors of the invention can include a chimeric gene which encodes anti-Fc receptor-TM fusion protein. Generally, the anti-Fc receptor (anti-FcR) portion of the fusion protein comprises an antibody or antibody fragment. In particular embodiments of the invention, expression vectors pJG717 encoding an H22 (anti-FcγR)-TM protein, and pJG718 encoding an A77 (anti-FcαR)-TM protein are employed to transform target cells.

It will be understood that a wide range of vectors, such as described below, can be used for recombinantly expressing genes (e.g., anti-FcR antibody-transmembrane protein fusion genes) in effector cells. Such vectors can be constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., *Molecular Cloning: A Laboratory Manual*, (Cold Spring Harbor Laboratory Press, Cold Spring Harbor, N.Y. [1989]). Practitioners of ordinary skill in the art are familiar with the standard resource materials as well as specific conditions and procedures. However, for convenience, the following paragraphs may serve as a guideline.

Any of the methods known to the art for the insertion of DNA fragments into a vector may be used to generate expression constructs of the present invention, including appropriate transcriptional/translational control signals. See, for example, Sambrook et al., supra; and Ausubel et al. eds. *Current Protocols in Molecular Biology*, (John Wiley & Sons, New York [1992]). These methods may include in vitro DNA recombinant and synthetic techniques and in vivo genetic recombination.

Anti-FcR antibody-transmembrane protein fusion genes of the present invention are typically operably linked to transcriptional regulatory sequences, such as promoters and/or enhancers, to regulate expression of the gene in a particular manner. In certain embodiments, the useful transcriptional regulatory sequences are those that are highly regulated with respect to activity, both temporally and spatially. Thus, the promoters of choice can be those that are active only in particular tissues or cell types. Where the promoter is obtained from a mammal, the mammal may be homologous (the same species as the mammal to be transformed) or non-homologous (a different species).

Appropriate promoters/enhancers can be introduced into vectors using standard methods in the art (see e.g., Maniatis). Any promoter that is sufficient to direct the initiation of transcription in a target cell may be used in the invention. For example, promoters/enhancers which may be used to control the expression of a recombinant gene include, but are not limited to, the native transcriptional regulatory sequences for the recombinant gene (e.g., the anti-FcR antibody transmembrane fusion gene regulatory sequences or the like), the cytomegalovirus (CMV) promoter/enhancer (Keating et al. (1990) *Exp Hematol* 19:99–102;1 and Karasuyama et al., 1989*, J. Exp. Med,* 169:13), the human β-actin promoter (Gunning et al. (1987) *PNAS* 84:4831–4835), the glucocorticoidinducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) *RNA Tumor Viruses, Cold Spring Harbor Laboratory, Cold Spring Harbor, N.Y.), the SV*40 early or late region promoter (Bernoist et al. (1981) *Nature* 290:304–310; Templeton et al. (1984) *Mol. Cell Biol.,* 4:817; and Sprague et al. (1983) *J. Virol.,* 45:773), the promoter contained in the 3' long terminal repeat of Rous sarcoma virus (RSV) (Yamamoto et al., 1980*, Cell,* 22:787797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics,* 1:379–384). A preferred non-tissue specific promoter is the CMV promoter (DeBernardi et al. (1991) *PNAS USA* 88:9257–61).

As an alternative to constitutive expression, the anti-FcR antibody-transmembrane protein fusion gene may be placed under the control of a cell specific promoter. Examples of these promoters include globin promoters, the granzyme A promoter for expression in T-cells and NK cells, the CD34 promoter for expression in stem and progenitor cells, the CD8 promoter for expression in cytotoxic T-cells, and the CD11b promoter for expression in myeloid cells.

Inducibe promoters may also be used for gene expression under certain physiologic conditions. Those skilled in the art will recognize a variety of inducible prokaryotic and/or eukaryotic promoters which can be used to control expression of a recombinant gene. For example, an IPTG-inducible promoter can be used to conditionally control expression of a recombinant gene. Another transcriptional control system is responsive to hormones (Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604).

The vectors useful for preparing the recombinant genes of this invention typically contain one or more additional elements useful for optimizing expression in a cell. The gene construct may include transcription termination elements, such as to direct polyadenylation of an mRNA transcript, as well as intronic sequences. For example the coding sequence of the recombinant gene can be flanked at its 3' end by SV40 sequences (SV40 intron/pA) which add the transcription termination and polyadenylation signals to the transcript. In yet other embodiments, the hematopoietic gene can include intronic sequence(s) interrupting the coding sequence. In many instances, transcription of a recombinant gene in mammals is increased by the presence of one or more introns in the coding sequence.

In still other embodiments, the fusion gene construct can include additional elements which facilitate its manipulation in cells (e.g., yeast, bacterial) prior to insertion in the intended recipient cell. For instance, the vector may include origin of replication elements for amplification in prokaryotic cells. The gene construct or vector can include selectable markers for isolating transformed cells in the presence of untransformed cells, generated in a host such as a yeast or a bacterial cell used for engineering or amplifying the construct or vector. Selectable marker genes can encode proteins necessary for the survival and/or growth of transfected cells under selective culture conditions. Typical selection marker genes encode proteins that, for example: (i) confer resistance to antibiotics or other toxins, e.g., ampicillin, tetracycline or kanomycin for prokaryotic host cells, and neomycin, hygromycin or methotrexate for mammalian cells; or (ii) complement auxotrophic deficiencies of the cell.

The gene construct may be administered to cells (e.g., target cells to be transformed) in any biologically effective carrier, e.g. any formulation or composition capable of effectively transfecting cells ex vivo or in vivo with the expression construct. Efficient DNA transfer methods are known in the art (see, for example, Keating et al. (1990) *Exp Hematol* 18:99–102; and Dick et al. (1986) *Trends Genet* 2:165). Approaches include insertion of the gene into viral vectors including recombinant retroviruses, adenovirus and adeno-associated viruses, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ co-precipitation of recipient cells and vector. Choice of the particular gene delivery system will depend on such factors as the phenotype of the cell. Another factor in the selection of the appropriate transfection formulation is the consideration raised by ex vivo transformation versus in vivo transformation, with the latter requiring consideration of the route of administration, e.g. locally or systemically.

One approach for either ex vivo or in vivo introduction of gene constructs of the present invention construct into cells is by use of a viral vector containing the gene as part of the virus genome carried within the virion particle. Infection of cells with a viral vector ("transduction") has the advantage that a large proportion of the targeted cells can receive the nucleic acid. Additionally, molecules encoded within the viral vector are expressed efficiently in cells which have taken up viral vector nucleic acid.

Retrovirus vectors are generally understood to be one of the recombinant gene delivery system of choice for the transfer of exogenous genes into stem cells, particularly into humans cells. (see e.g., Hawley R. G., et al (1994) *Gene Therapy* 1: 136–38)). These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses as a gene delivery system, and defective retroviruses are well characterized for use in gene transfer for gene therapy purposes (for a review, see Miller, A. D. (1990) *Blood* 76:271). Thus, recombinant retrovirus can be constructed in which a part of the retroviral coding sequence (gag, pol env) essential to viral replication has been replaced by the anti-FcR transmembrane fusion protein gene of the invention, rendering the retrovirus replication defective. The replication defective retrovirus is then packaged into virions which can be used to infect a target cell through the use of a helper virus by standard techniques. Protocols for producing recombinant retroviruses and for infecting cells ex vivo or in vivo with such viruses can be found in Ausubel et al., supra, Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ΨCrip, ΨCre, Ψ2 and ΨAm.

Retroviruses have been used to introduce a variety of genes into many different cell types, including embryonic stem cells, bone marrow cells, lymphocytes, hepatocytes, by both ex vivo and in vivo protocols (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Exemplary retroviral vectors have been described that yield a high titre virus capable of efficiently transducing and expressing genes in undifferentiated embryonic and hematopoietic cells (Hawley et al (1994) *Gene Therapy* 1: 136–38). These vectors contain a selectable marker (neo, hph or pac) under the transcriptional control of an internal murine pgk promoter and unique restriction sites for insertion of genes downstream of a variant LTR from the retroviral mutant PCMV (PCC4 embryonal carcinoma cell-passaged myeloproliferative sarcoma virus). A variant of the above-described retroviral vectors, the Murine Stem Cell Virus (MSCV), is illustrated in the examples set out below.

The infective spectrum of retroviruses, and consequently of retroviral-based vectors, can be limited by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for stem cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector into an amphotropic vector.

To further illustrate, an anti-FcR antibody-transmembrane fusion gene construct can be generated using a retroviral vector which encodes a second fusion protein including the viral envelope protein and the vesicular stomatitis virus (VSV-G) glycoprotein (Burns et al. (1993) *Proc. Natl. Acad. Sci. USA* 90:8033–37; PCT Patent Application WO 92/14829; and WO 96/09400). Unlike typical amphotropic env proteins, the VSV-G protein is thought to mediate viral infection by fusing with a phospholipid component of cell membranes rather than by recognition of a cell surface protein. Since infection is not dependent on a specfic receptor, VSV-G pseudotyped vectors have a broad host range. CD34+/Thy-1+mobilized peripheral blood cells have previously been demonstrated to be transduced with high efficiency by a VSV-G pseudotyped retroviral vector (see Kerr et al. PCT publication WO 96/09400). Genetic modification of the stem cells with a anti-FcR antibody transmembrane fusion gene construct can be accomplished at any point during their maintenance by transduction with VSV-G pseudotyped virion containing the expression construct.

Moreover, use of retroviral gene delivery can be further enhanced by the use of tissue- or cell-specific transcriptional regulatory sequences which control expression of the recombinant anti-FcR antibody transmembrane fusion gene.

Another viral gene delivery system useful in the present invention utilizes adenovirus-derived vectors. The genome of an adenovirus can be manipulated such that it encodes the anti-FcR antibody transmembrane fusion gene product of interest, but is inactive in terms of its ability to replicate in a normal lytic viral life cycle (see, for example, Berkner et al. (1988) *BioTechniques* 6:616; Rosenfeld et al. (1991) *Science* 252:431–434; and Rosenfeld et al. (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are relatively stable and amenable to purification and concentration, and as above, can be modified so as to affect the spectrum of infectivity with respect to stem cell populations.

Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in *Methods in Molecular Biology*, E. J. Murray, Ed. (Humane, Clifton, N.J., 1991) vol. 7. pp. 109–127). Expression of the inserted anti-FcR antibody transmembrane fusion gene can be under control of, for example, the E1A promoter, the major late promoter (MLP) and associated leader sequences, the E3 promoter, or exogenously added promoter sequences.

Yet another viral vector system useful for delivery of anti-FcR antibody-transmembrane fusion genes is the adeno-associated virus (AAV). Adeno-associated viral vectors have been shown to be effective at transducing other genes into pluripotent anti-FcR antibody transmembrane fusion stem cells in vitro (see PCT Application WO 96/08560). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro and Immunol. (*1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to a recombinant anti-FcR antibody transmembrane fusion gene into stem cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081, Wondisford et al. (1988) *Mol. Endocrinol.* 2:32–39, Tratschin et al. (1984) *J. Virol.* 51:611–619; and Flotte et al. (1993) *J. Biol. Chem.* 268:3781–3790).

Anti-Fc Receptor Binding Components

As previously described, anti-Fc receptor binding components of the present invention include antibodies, functional antibody fragments (i.e., which retain binding capacity or the ability to recognize a particular epitope), peptides which mimic antibody binding and other Fc receptor binding agents. In a preferred embodiment, the Fc receptor binding component is expressed as a fusion protein which, when expressed by a target cell, comprises a portion which is exposed on the surface of the target cell and a portion which is inserted in the membrane of the cell (i.e., a transmembrane portion which favors a lipid environment). When expressed in this manner, the Fc receptor binding component is anchored to the target cell via the transmembrane portion. In one embodiment, the fusion protein comprises an antibody portion and a transmembrane domain portion. In particular embodiments, the antibody portion is derived from monoclonal antibodies referred to as H22 (anti-Fc$\gamma$R) and A77 (anti-Fc$\alpha$R) described herein.

The term "antibody" as used herein refers to immunoglobulin molecules and immunologically active determinants of immunoglobulin molecules, i.e., molecules that contain an antigen binding site which specifically binds (immunoreacts with) an antigen, such as an Fab or single chain Fv fragment. Nucleic acids encoding anti-FcR antibodies suitable for use in the present invention (i.e., which can be used to transform target cells) are available in the art (e.g., from the American Type Culture Collection, Rockville, Md., or commercially, e.g., from Becton-Dickinson or Immunotech), or can be prepared by standard techniques. Accordingly, the following is an overview of such techniques. For purposes of clarity, most of these techniques are referred to in terms of preparing antibodies and antibody fragments, instead of the preparing nucleic acids (e.g., genes) encoding antibodies and antibody fragments. However, it is known to those of ordinary skill in the art that once an antibody with a set of desired (e.g., anti-FcR) binding characteritics is prepared, the antibody can be sequenced and/or cloned using art recognized techniques (e.g., PCR) to provide a nucleic acid encoding the antibody.

Structurally, the simplest naturally occurring antibody (e.g., IgG) comprises four polypeptide chains, two copies of a heavy (H) chain and two of a light (L) chain, all covalently linked by disulfide bonds. Specificity of binding in the large and diverse set of antibodies is found in the variable (V) determinant of the H and L chains; regions of the molecules that are primarily structural are constant (C) in this set.

The binding sites of the proteins that comprise an antibody, i.e., the antigen-binding functions of the antibody, are localized by analysis of fragments of a naturally-occurring antibody. Thus, antigen-binding fragments are also intended to be designated by the term "antibody."

Examples of binding fragments encompassed within the term antibody include: a Fab fragment consisting of the $V_L$, $V_H$, $C_L$ and $C_{H1}$ domains; an Fd fragment consisting of the $V_H$ and $C_{H1}$ domains; an Fv fragment consisting of the $V_L$ and $V_H$ domains of a single arm of an antibody; a dAb fragment (Ward et al., 1989 Nature 341:544–546) consisting of a $V_H$ domain; an isolated complementarity determining region (CDR); and an F(ab')$_2$ fragment, a bivalent fragment comprising two Fab' fragments linked by a disulfide bridge at the hinge region. These antibody fragments are obtained using conventional techniques well-known to those with skill in the art, and the fragments are screened for utility in the same manner as are intact antibodies.

An anti-FcR "antibody" of the invention can further include a bispecific molecule or chimeric molecule having at least one antigen binding determinant derived from an anti-FcR antibody, or a single chain anti-FcR antibody. Although the H and L chains are encoded by separate genes, a synthetic linker can be made that enables these chains to be made as a single protein chain (known as single chain antibody, sc-Ab), or to be recombinantly expressed as a single protein chain (Bird et al. 1988 Science 242:423–426; and Huston et al. 1988 PNAS 85:5879–5883).

The term "monoclonal antibody" or "monoclonal antibody composition" as used herein refers to a preparation of antibody molecules of single molecular composition. A monoclonal antibody composition displays a single binding specificity and affinity for a particular epitope. Monoclonal antibodies can be prepared using a technique which provides for the production of antibody molecules by continuous growth of cells in culture. These include but are not limited to the hybridoma technique originally described by Kohler and Milstein (1975, Nature 256:495–497; see also Brown et al. 1981 J. Immunol 127:539–46; Brown et al., 1980, J Biol Chem 255:4980–83; Yeh et al., 1976, PNAS 76:2927–31; and Yeh et al., 1982, Int. J. Cancer 29:269–75) and the more recent human B cell hybridoma technique (Kozbor et al., 1983, Immunol Today 4:72), EBV-hybridoma technique (Cole et al., 1985, Monoclonal Antibodies and Cancer Therapy, Alan R. Liss, Inc., pp. 77–96), and trioma techniques.

A monoclonal antibody can be produced by the following steps. In all procedures, an animal is immunized with an antigen such as a protein (or peptide thereof) as described above for preparation of a polyclonal antibody. The immunization is typically accomplished by administering the immunogen to an immunologically competent mammal in an immunologically effective amount, i.e., an amount sufficient to produce an immune response. Preferably, the mammal is a rodent such as a rabbit, rat or mouse. The mammal is then maintained on a booster schedule for a time period sufficient for the mammal to generate high affinity antibody molecules as described. A suspension of antibody-producing cells is removed from each immunized mammal secreting the desired antibody. After a sufficient time to generate high affinity antibodies, the animal (e.g., mouse) is sacrificed and antibody-producing lymphocytes are obtained from one or more of the lymph nodes, spleens and peripheral blood. Spleen cells are preferred, and can be mechanically separated into individual cells in a physiological medium using methods well known to one of skill in the art. The antibody-producing cells are immortalized by fusion to cells of a mouse myeloma line. Mouse lymphocytes give a high percentage of stable fusions with mouse homologous myelomas, however rat, rabbit and frog somatic cells can also be used. Spleen cells of the desired antibody-producing animals are immortalized by fusing with myeloma cells, generally in the presence of a fusing agent such as polyethylene glycol. Any of a number of myeloma cell lines suitable as a fusion partner are used with to standard techniques, for example, the P3-NS1/1-Ag4-1, P3-x63-Ag8.653 or Sp2/O-Ag14 myeloma lines, available from the American Type Culture Collection (ATCC), Rockville, Md.

The desired hybridomas obtained from among the fused cells are cultured in selective medium such as HAT medium, designed to eliminate unfused parental myeloma or lymphocyte or spleen cells. Hybridoma cells are selected and are grown under limiting dilution conditions to obtain isolated clones. The supernatants of each clonal hybridoma is screened for production of antibody of desired specificity and affinity, e.g., by immunoassay techniques to determine the desired antigen such as that used for immunization. Monoclonal antibody is isolated from cultures of producing cells by conventional methods, such as ammonium sulfate precipitation, ion exchange chromatography, and affinity chromatography (Zola et al., Monoclonal Hybridoma Antibodies: Techniques And Applications, Hurell (ed.), pp. 51–52, CRC Press, 1982). Hybridomas produced according to these methods can be propagated in culture in vitro or in vivo (in ascites fluid) using techniques well known to those with skill in the art.

For therapeutic use of antibodies of non-human origin in humans, the non-human "foreign" epitopes elicit immune response in the patient. If sufficiently developed, a potentially lethal disease known as HAMA (human antibodies against mouse antibody) may result. To eliminate or minimize HAMA, it is desirable to engineer chimeric antibody derivatives, i.e., "humanized" antibody molecules that combine the non-human Fab variable region binding determinants with a human constant region (Fc). Such antibodies are characterized by equivalent antigen specificity and affinity of monoclonal and polyclonal antibodies described above, and are less immunogenic when administered to humans, and therefore more likely to be tolerated by the patient.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559.)

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science 229:1202–1207 and by Oi et al., 1986, BioTechniques 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 *Nature* 321:552–525; Verhoeyan et al. 1988 *Science* 239:1534; and Beidler et al. 1988 *J Immunol.* 141:4053–4060).

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, *Humanized Antibodies to Fc Receptors for Immunoglobulin G on Human Mononuclear Phagocytes.*

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or subsituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Human monoclonal antibodies (HumAb antibodies) directed against human proteins can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Bruggeman et al. 1991 *Eur J Immunol* 21:1323–1326).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FRI) sequences, as well as primer to a conserved 3' constant region primer can be used for PCR amplification of the heavy and light chain variable regions from a number of murine antibodies (Larrick et al., 1991, *Biotechniques* 11:152–156). A similar strategy can also been used to amplify human heavy and light chain variable regions from human antibodies (Larrick et al., 1991, *Methods: Companion to Methods in Enzymology* 2:106–110).

In an illustrative embodiment, RNA is isolated from B lymphocytes, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combinantion, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the *Pharmacia Recombinant Phage Antibody System*, catalog no. 27-9400-01; and the Stratagene SurfZAP™ phage display kit, catalog no. 240612), examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No.

WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4\text{-}Ser)_3$ linker can be used to produce a single chain antibody which can render the display package separable based on antigen affinity. Isolated scFv antibodies immunoreactive with the antigen can subsequently be formulated into a pharmaceutical preparation for use in the subject method.

Once displayed on the surface of a display package (e.g., filamentous phage), the antibody library is screened with the FcγR, or peptide fragment thereof, to identify and isolate packages that express an antibody having specificity for the FcγR. Nucleic acid encoding the selected antibody can be recovered from the display package (e.g., from the phage genome) and subcloned into other expression vectors by standard recombinant DNA techniques.

Immune response to "foreign" antigens comprises the notion that "self" proteins and other molecules expressed within an organism are not antigenic or immunogenic to that organism. In fact, discrimination between isologous or homologous determinants and "foreign," or heterologous determinants is achieved through maturation of the immune system of an organism during development of the immune system. A system of selection against immune cells bearing antibodies with binding determinants to "self" occurs, so that when mature the immune system does not attack proteins or other molecules native to the organism. In certain pathological conditions known as "autoimmune diseases," however, such discrimination is not as accurate, and endogenous structures may be subject to attack from the immune system. Examples of autoimmune diseases and conditions in which there is autoimmune exacerbation of symptoms include systemic lupus erythematosus, myasthemia gravis, multiple sclerosis, and rheumatoid arthritis. One autoimmune disease, idiopathic thrombocytopenic purpura (ITP), which affects approximately 150,000 patients in the United States (according to the U.S. Department of HHS, 1992 data), results from macrophages in the spleen and liver removing autoantibody-coated platelets from circulation. The autoantibodies generally have the IgG isotype (Schwarz, R. S., Autoimmunity and Autoimmune Diseases, 1993, p. 1075. In: Fundamental Immunology, 3rd Ed., W. E. Paul, Ed., Raven Press, NY), and the disease results in continuous platelet destruction.

Other Fc receptor binding components include peptides which mimic the binding of anti-Fc receptor antibodies of the invention, such as antibodies H22 and A77 described herein. Such "peptide mimetics" can be dessigned and generated by those of ordinary skill in the art according to known techniques, such as those described by Saragovi et al. (1991) *Science* 253:792; Hinds et al. (1991) *J. Med. Chem.* 34(6):1777; Jenks et al. (1992) *J. Natl Cancer Inst.* 84:79; and Fassine et al. (1994) *Immunomethods* 5:121.

Fc Receptors

Fc receptors are divided among four classes known as Fcγ receptor, Fcα receptor, Fcμ receptor, Fcε receptor) which bind to IgG, IgA, IgM, IgE, respectively.

Receptors for IgG molecules, in particular, are known as FcγR, of which FcγRI is a high affinity receptor found on dendritic cells, monocytes and macrophages, and are inducible on neutrophils and eosinophils (Van de Winkel J G I, et al., 1993, *Immunol Today* 14:215). The lower affinity IgG receptors are FcγRII, found on neutrophils (polymorphonuclear neutrophils, PMNs), monocytes, and platelets, and FcγRIII, found on macrophages, PMNs, and natural killer cells (NKs). The low affinity IgG receptors are also found on mast cells and subsets of T cells (Ravetch et al., 1991, *Ann. Rev.* 1 mm. 9:457). Biological functions associated with binding of IgG to these receptors include phagocytosis, superoxide generation, cytotoxicity, and triggering mediator release. The biological role of FcγRI has not been fully determined, since because of its high affinity it might be saturated with IgG in vivo, suggesting a steady state situation. Data including induction of expression of FcγRI during streptococcal infection (Guyre, P. M et al., 1990, *J. Clin. Invest.* 86:1892), induction during IFN-γ treatment of patients with chronic granulomatous disease, and on neutrophils from a neglible quantity in healthy individuals to a large number during acute inflammation (Davis, B H et al., supra) suggest an important role in resistance to infection (Van de Winkel J G I, et al., 1993, *Immunol Today* 14; 215).

Effector Cells and Antigen Presentation

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. In preferred embodiments, an effector cell is capable of inducing antibody-dependent cellular toxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of Fcγ RI-bearing cells against targets. An effector cell can phagocytose a target antigen or a target cell. An effector cell can also lyse a target cell.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

Using the methods and compositions provided herein, effector cells are targeted to cells associated with (e.g., which naturally or recombinantly express) a target antigen. For example, effector cells can be directed via their Fc receptors to a tumor cells, such as TAG-72-bearing cells.

Exemplary TAG-72-bearing cells include carcinoma or adenocarcinoma-derived cells (e.g., colon, breast, prostate, ovarian and endometrial cancer cells) (Thor, A. et al. (1997) *Cancer Res* 46: 3118; Soisson A. P. et al. (1989) *Am. J. Obstet. Gynecol.* :1258–63). Alternatively, effector cells can be directed via their Fc receptors to cells infected with a pathogen, such as HIV-1.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, ovarian carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Antigen uptake through antigen-antibody complexes bound to Fc receptors for IgG (Fc γR) increases the efficiency of antigen presentation and thereby antigen-specific T-cell activation by human and mouse macrophages, (Celis et al (1984) Science 224:297–299; Chang (1985) Immunol. Today 6:245–259; Manca et al. (1988) Immunol. 140:2893–2898; Schalke et al. (1985) J. Immunol. 134:3643–3648; and Snider et al (1987) J. Immunol. 139:1609–1616). The binding of these complexes to FcγR is mediated by the Fc region of the antibody. This binding is susceptible to inhibition by physiological concentration of IgG.

An optimal antibody response to a thymus-dependent antigen requires that the B cell obtain help from CD4+ helper T cell. The B cell is uniquely designed to accomplish this in that it contains antigen-specific immunoglobulin on its surface which allows it to bind, internalize and process antigen for presentation very efficiently. Other antigen presenting cells, such as the macrophage and dendritic cell, lack antigen-specific receptors, and therefore also lack this highly efficient mechanism for processing and presenting antigen. However, the apparent requirement for adjuvants when administering vaccines suggests a need for an antigen presenting cell in addition to the B cell. Also, it appears that antigen presentation by resting B cells to resting T cells does not lead to a T cell activation, but rather to T cell tolerance (Eynon et al. (1992) J. Esp. Med. 175:131). This is due to the failure of the resting B cell to deliver all the signals required for activation of the resting T cell. On the other hand, it appears that induction of T cell tolerance by the resting B cell could be averted if the resting T cell first responds to antigen on the antigen presenting cell such as the macrophage or dendritic cell (Parker et al. (1991) FASEB J. 5:2777). This implies that in the naive individual, the resting T cell must first interact with a macrophage or dendritic cell before interacting with the resting B cell.

These considerations have lead to the conclusion that the optimal immunogen requires two major components: antigen which can be recognized by the antigen-specific B cell; and a component which directs antigen for efficient processing and presentation to an antigen presenting cell other than the resting B cell (Parker et al., ibid.; Germain (1991) Nature 353:605). Attaching antigens to anti-Fc receptor antibodies satisfies these criteria since antigen directed to Fc receptors on the macrophage enhances antigen presentation at least 100 fold (Immunol. Today (1985) 6:245). Studies performed in vivo support the efficacy of such a vaccine. For example, a substantial increase in antibody production has been observed following immunization of mice with bispecific antibody which directed antigen to MHC class II or FcγRII (Snider et al. (1990) (J. Exp. Med. 171:1957–1963). In addition, the requirement for adjuvant was eliminated. The ability to use substantially lower doses of immunogens is especially valuable when administering immunogens such as allergens that are potentially toxic at higher doses. Tolerance against some allergens can be obtained by repeated low dose administration of the allergen.

To construct an immunogen for human use which would satisfy the above criteria, the observation that antigen-antibody complexes can significantly enhance antigen presentation was expanded. When antigen-antibody complexes bind to an FcR (e.g., FcγR or FcαR) on the monocyte or macrophage, the antigen is internalized and its subsequent presentation and thus T cell activation, is dramatically enhanced in vitro (Chang (1985) Immunol. Today 6:245), decreasing the antigen concentration required for T cell activation by 10 to 100-fold. The data presented here demonstrate the potential for using FcR-targeted immunogens and target cells as vaccines and to enhance antigen presentation.

In the methods of this invention, antigens expressed within or on the surface of a target cell can be targeted to an antigen-presenting cell to enhance the processes of internalization and presentation by these cells, and ultimately, to stimulate an immune response therein.

Preferred surface receptors of antigen-presenting cells for targeting are the receptors for the Fc region of IgG (FcγR). These receptors mediate internalization of antibody-complexed antigens. The Fcγ receptors include FcγRI, FcγRII, and FcγRIII. The most preferred target is the high affinity Fc receptor (FcγRI).

Other preferred Fc receptors which may be targeted include Fcα receptors. Binding of ligand to FcαR triggers phagocytosis and and antibody mediated cell cytotoxicity in leukocytes and FcαR-bearing cell lines. Fcα receptors can also cooperate with receptors for IgG on effector cells in enhancing the phagocytosis of target cells. Monoclonal antibodies of the IgM (Shen, L. et al., 1989 *J. Immunol.* 143: 4117) and IgG (Monteiro, R. C. et al., 1992 *J. Immunol,* 148: 1764) classes have been developed against FcαR.

The production and characterization of monoclonal antibodies which bind FcγRI without being blocked by human IgG are described by Fanger et al. in PCT application WO 88/00052 and in U.S. Pat. No. 4,954,617, and in U.S. Pat. No. 5,635,600, the teachings each of which are incorporated by reference herein. These antibodies bind to an epitope of Fcγ RI which is distinct from the Fc binding site of the receptor and, thus, their binding is not blocked substantially by physiological levels of IgG. Specific anti-FcγRI antibodies useful in this invention are mAb 22, mAb 32, mAb 32.2, mAb 44, mAb 62 and mAb 197. The hybridoma producing mAb 32.2 (an identical sub-clone of mAb 32) is available from the American Type Culture Collection, Rockville, Md., ATCC No. HB9469.

Antibody preparations suitable for directing the cell or virus displaying an anti-FcαR binding determinant to an effector all displaying FcαR have been described (Monteiro et al. 1992, J. Immunol. 148:1764–1770; and U.S. Ser. No. 08/678,194, which is hereby incorporated by reference). Monteiro et al. describe mAb A77 and A3, which specifically bind FcαR at an epitope such that binding is not inhibited by human IgA.

Pharmaceutical Compositions

The Examples below are not intended as delimiting with respect to the nature of the therapeutic agent such as a vector or a genetically modified cell, or to a particular route of the administration and additional routes are listed herein, infra.

In another embodiment of the present invention, the compositions of the invention (e.g., expression vectors and transformed (targeted) cells) can be administered by combination therapy, i.e., combined with other agents. For example, the combination therapy can include a composition of the present invention with at least one other vector or a genetically modified cell, at least one antibiotic, or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The phrases "parenteral administration" and "administered parenterally" as used herein means modes of administration other than oral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

When administered in vivo, transformed cells and expression vectors of the present invention can be administered (e.g., as a pharmaceutical composition) to subjects using a variety of methods known in the art. As will be appreciated by the skilled artisan, the route and/or mode of administration will vary depending upon the desired results.

Dosage regimens are adjusted to provide the optimum desired response (e.g., a therapeutic response, such as protective immunity against tumor cells or a pathogen). For example, a single bolus can be administered, several divided doses can be administered over time or the dose can be proportionally reduced or increased as indicated by the exigencies of the therapeutic situation.

One of ordinary skill in the art can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intramuscular, intraperitoneal, or subcutaneous.

Uses and Methods

The compositions and methods of the present invention can be used to achieve targeted immunostimulation (e.g., against target antigens or target cells) either in vitro or in vivo.

For in vitro use, immunocompetent effector cells are separated and purified from patient blood. These effector cells are then contacted in culture with the antigen in association with a cell or virus displaying the FcR binding determinant. The antigen-presenting effector cells will process the antigen and present fragments on their surface. When immune cells, such as T and B lymphocytes are present, an antigen-specific immune response can be stimulated.

Alternatively, target cells associated with an antigen can be transformed to express an FcR binding component ex vivo and then returned to patients to elicit a specific effector cell-mediated immune response via the above-summarized process. The cells are administered in a pharmacologically acceptable solution at a dosage which will evoke an immune response against the antigen. The cells may be irradiated prior to administration to remove the possibility of the transformed cells growing inside the patient. Further, the patient's cells (e.g. blood cells) may be removed, fractionated and cultured if appropriate to expand the cell number, treated ex vivo and returned to the patent for therapy. Further, ex vivo cultured cells may be treated at various points during ex vivo culture and expansion, with agents to modify expression or activity of certain functional anti-FcR binding components. Agents include but are not limited to, growth factors, cytokines, lymphokines such as IFN-γ, G-CSF, TNF, and GM-CSF, and interleukins such as IL-2, IL-10 and IL-12.

The optimum dose of cells, as well as the molar ratio of antigen and binding agent, may vary dependent upon factors such as the type of antigen, the immune status of the host, the type of tumor or infection or other disease being treated, etc. In most cases, the does of cells required to elicit an immune response (as determined by any standard method for assessment of immune response) should be lower than that which would be required if the antigen were given alone or as a complex with a monospecific antibody for the antigen (Snider et al., ibid.).

The methods provided by the present invention can be used to enhance or reinforce the immune response to an antigen or to multiple antigens simultaneously. For example, the methods can be used to treat chronic infections, such as hepatitis and AIDS, where the unaided immune systems is unable to overcome the infection. The methods can also be used to treat acute stages of infection when reinforcement of an immune response against the invading organism may be necessary.

The methods can further be used to reduce the dose of antigen required to obtain a protective or therapeutic immune response or in instances when the host does not respond or responds minimally to the antigen. Although generally desirable, the lowering of effective dose can be especially desirable when the antigen is toxic to the host such as is the case for allergies.

The methods can also be used in disease therapy for cancer. For example, transformed cells of the invention can be used to target tumor-associated (or tumor-specific) antigens or tumor cells to antigen-presenting cells in order to cause or to enhance an immune response against the tumor. Importantly, the tumor antigen(s) need not be known, as the whole tumor cell is targeted to the effector cell. Indeed, many tumor cells express several different tumor-specific specific antigens. In a preferred embodiment, transformed target cells of the invention are cancer cells, particularly cancer cells from breast, ovary, testis, lung, colon, rectum, pancreas, liver, central nervous system, head and neck, kidney, bone, blood and lymphatic system cancers. Suitable target antigens among such cancer cells include members of the human EGF-like receptor family, such as EGF receptor, the cancer cell antigens HER-2/neu, HER-3, HER-4, and a heteromultimeric receptor comprised of at least one HER subunit. Additional cancer cell antigens include carcinoembryonic antigen, gastrin releasing peptide receptor antigen, and TAG 72. TAG 72 has been identified on about 90% of colorectal cancers, 85% of breast tumors, and 95% of ovarian tumors (Johnson et al.(1986) *Cancer Res.* 46:850–897; Bodmer, M. et al., European Patent Specification 0 348 442 B 1; Mezes, P. et al. International Application WO 93/12231).

In another embodiment, transformed cells of the invention target infectious disease antigens to effector cells. Infectious disease antigens include those from bacteria, fungi, protozoa, and viruses, such as HIV, HTLV and FELV, protozoan (such as Toxoplasma gondii), fungal (such as *Candida albicans*); and bacterial (such as *Staphylococcus aureus, Streptococcus hemolyticus* and *Mycobacterium tuberculosis*).

Another type of antigen which can be targeted by way of the present invention is an allergen. An "allergen" refers to a substance that can induce an allergic or asthmatic response in a susceptible subject. The number of allergens that elicit a sensitive response in a proportion of a population is enormous, and includes pollens, insect venoms, animal dander, dust mite proteins, fungal spores and drugs (e.g. penicillin). Examples of natural animal and plant allergens include proteins specific to the following genera: Felis (*Felis domesticus*); Canis (*Canis familiaris*); Dermatophagoides (*e.g. Dermatophagoides farinae*); Periplaneta (e.g. *Periplaneta americana*); Ambrosia (*Ambrosia artemiisfolia*; Lolium (e.g. *Loliumperenne or Lolium multiflorum*); Cryptomeria (*Cryptomeria japonica*); Alternaria (*Alternaria alternata*); Alder; Alnus (*Alnus gultinosa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*) Thuya (e.g. *Thuya orientalis*); Chamaecyparis (e.g. *Chamaecyparis obtusa*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poapratensis or Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

Many allergens are found in airborne pollens of ragweed, grasses, or trees, or in fungi, animals, house dust, or foods. As a class, they are relatively resistant to proteolytic digestion. Preferable allergens are those which bind to IgE on mast cells and basophils, thereby causing a range of symptoms from inflammation and asthma to a type I anaphylaxis hypersensitivity reaction.

The methods of the present invention can also be used to vaccinate against diseases and cancers by including by causing "redirected" targeted immunostimulation against antigens associated with such diseases and cancers. Breast and ovarian cancers are sex hormone dependent cancers. Breast tumors may be characterized by abnormally expressed receptors, e.g. those of the human-EGF-like receptor family (HER), for example HER-2, -3, and 4. The invention is not limited to these embodiments of HER antigens. The natural HER ligand, heregulin, can be incorporated into a bispecific antibody (BsAb) or multispecific molecule, as a means to target a breast tumor cell expressing one or more HER receptor during cancer. Further, heregulin molecules are binding determinants for heterodimeric HER receptors containing, eg. a monomer of each of HER-2, -3 or -4 in combination.

Additional examples of sex hormone-dependent cancer include prostate cancer (Smith, P. (1995), *Cancer Surveys Vol. 23: Preventing Prostate Cancer*, Imper. Cancer Research Fund and testicular cancers). The growth of hormone-dependent cancer types is promoted by male hormones (e.g., androgens such as testosterone and dihydrotestosterone). Removal of the testes (castration) was for many years the standard method of preventing secretion of male hormones by the gonads, to reduce growth of the cancer. Currently, secretion of male hormones is suppressed by chemical means by interfering with production of luteinizing hormone (LH), which regulates synthesis of male hormones. Similar considerations are applicable to other sex hormone-dependent cancers, such as breast or ovarian cancer, so that patients with these diseases or in a population prone to these diseases, are usually not administered sex hormones as therapeutic or replacements.

In one embodiment, the nestin protein for brain cancers and which is expressed during normal mammalian fetal development, and is also expressed on tumors of the central nervous system, including most forms of brain cancer (McKay, D. G. Ronald, U.S. Pat. No. 5,338,839, Aug. 16, 1994) is used as a target antigen. Nestin is also expressed on melanomas on the skin and on melanomas that have metastasized (V. A. Florenes, R. Holm, O. Myklebost, U. Lendahl, O. Fodstad, *Cancer Res.* 54: 354–6, 1994), to other organs and are difficult to detect and treat. The preferred site of delivery for treatment of a brain tumor with the molecules of this invention is directly into the central nervous system or directly, to the brain via spinal injection or fine needle delivery. For a metastatic cancer, a preferred delivery route would be by direct injection into the circulation, or by the ex vivo blood methods described herein.

Other tumor types include Wilm's tumor (A. J. Buckler, K. M. Call, T. M. Glaser, D. A. Haber, D. E. Housman, C. Y. Ito, J. Pelletier, Rose, E. A. Rose, U.S. Pat. No. 5,350,840) a pediatric kidney cancer due to occurrence of a somatic mutation in the patient's single copy of a gene normally found in two intact copies. Wilm's tumor can be cured surgically in 95% of cases, and a bispecific or multispecific multivalent binding protein is envisioned to be suitable as an adjunct therapeutic modality for surgical patients. Other examples of known cancer-associated proteins for which the compositions of matter and methods of the current invention are suitable include those associated with gastrointestinal cancer (R. Fishel et al, International Application WO 95/14085, 05/26/95), those characterized by development of multiple drug resistance during chemotherapy (J. M. Croop et al., U.S. Pat. No. 5,198,344), and a large number of oncogenes well known to the skilled artisan such as Rb, ras, and c-myc, the sequences of which are available for analysis to those with skill in the art.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below.

The invention is further illustrated by the following examples, which should not be construed as further limiting. In addition, the materials, methods, and examples are illustrative only and not intended to be limiting. The contents of all references, pending patent applications and published patents, cited throughout this application, are hereby expressly incorporated by reference.

EXAMPLES

Materials and Methods

The following methodology described in the Materials and Methods section was used throughout the Examples, set forth below.

Cell Lines and Monoclonal Antibodies

The anti-Fcγ receptor antibody is a humanized form of monoclonal antibody 22 (H22), described in U.S. Pat. No. 5,635,600, which is incorporated by reference. The production and characterization of the H22 antibody is described in Graziano, R. F. et al. (1995) *J. Immunol* 155 (10): 4996–5002 and PCT/US93/10384. The H22 antibody producing cell line was deposited at the American Type Culture Collection on Nov. 4, 1992 under the designation HA022CL 1 and has the ATCC accession number CRL 11,177.

Other specific anti-FcγRI antibodies useful in this invention are mAb 32.2, mAb 44, mAb 62 and mAb 197. The hybridoma producing mAb 32.2 is available from the American Type Culture Collection, ATCC accession number HB9469.

The murine hybridoma producing cell line for the anti-FcαR antibody is exemplified by A77 (Monteiro et al. 1992, J. Immunol. 148: 1764–1770).

The anti-FcR mAbs were purified from each respective hybridoma supernatant by protein A affinity chromatography (Bio-Rad, Richmond, Calif.).

Preparation of Blood Cells

Leukocytes were prepared from heparinized whole venous blood or from apheresis of normal human volunteers. Whole blood was diluted with RPMI containing 5% dextran at a ratio of 2.5:1 (v/v). The erythrocytes were allowed to sediment for 45 minutes on ice, then the cells in the supernatant were transferred to a new tube and pelleted by centrifugation. The residual erythrocytes were removed by hypotonic lysis. The remaining lymphocytes, monocytes and neutrophils were kept on ice until use in binding assays. For some experiments, neutrophils were separated from mononuclear cells by ficoll hypaque (Pharmacia-Upjohn, Piscataway, N.J.) gradient separation. Monocytes were enriched from mononuclear cells by cold aggregation and settling through a cushion of fetal calf serum. Monocyte cultures were used fresh or were incubated at 37° C., 5% $CO_2$ for 24 to 48 hours in teflon dishes at $4\times10^6$ cells/ml of MSFM containing 2.0% normal human serum type AB (Sigma, St. Louis, Mo.) and 500 IRU/ml IFN-γ (R&D Systems, Minneapolis, Minn.). Neutrophils were cultured for 24 to 48 hours (37° C., 5% $CO_2$) in AIM V media (Gibco/BRL, Grand Island, N.Y.) with 50 ng/ml G-CSF (Kindly provided by R. Repp, U. of Erlanger, Germany) and 500 IRU/ml IFN-γ.

Binding by Flow Cytometry

The binding of anti-idiotype antibody (22 ID) or soluble FcγRI (ligand) to H22-TM displayed on transformed cells was assessed by flow cytometry. Various concentrations of fluorescent antibody or sFc diluted in PBS, pH 7.4 containing 2 mg/ml BSA and 0.05% $NaN_3$ (PBA), were incubated with transformed NSO cells or with transformed MTC cells for one hour at 0° C. The cells were washed with PBA and incubated with a phycoerythrin labeled goat anti-mouse antibody for one hour at 0° C. The cells were washed and fixed with 1% paraformaldehyde, and cell associated fluorescence was analyzed on a Becton Dickinson (Mountain View, Calif.) FACScan.

Example 1

Preparation of a Plasmid Expression Vector for Surface Expression of Single Chain Antibody Specific for FcγR A plasmid expression vector (FIG. 1) to direct surface expression of the single chain antibody portion (sFv) of anti-FcγRI mAb H22 was engineered by inserting a DNA fragment encoding the H22 sFv in frame with the sequence for the transmembrane domain of platelet derived growth factor receptor (PDGF-R) using a commercial plasmid vector pDisplay (Invitrogen, Inc., 1600 Faraday Ave, Carlsbad, Calif. 92008; Cat. No. V660-20$210). pDisplay is a 5,325 base pair mammalian expression vector that is designed to target recombinant proteins to the surface of mammalian cells via the transmembrane domain of PDGF-R. An H22 sFv fragment protein was targeted and anchored to the surface of recipient cells (NSO and MTC cells) by cloning a DNA encoding the H22 sFv fragment in frame with the N-terminal cell surface targeting signal and the C-terminal transmembrane anchoring domain of PDGF-R, encoding fusion protein H22-TM The pDisplay plasmid features: a CMV promoter (bases 1–596); a T7 promoter/priming site for in vitro transcription of sense RNA and for sequencing of inserts (bases 638–657); the murine IgK-chain V-J2-C signal peptide (bases 737–799); hemagglutinin A epitope (bases 800–826); multiple cloning site including sites SfiI, BglI, XmaI, SacII, PstI, SalI and AccI (bases 827–873); myc epitope (bases 874–903); PDGF-R transmembrane domain (bases 907–1,056); bovine growth hormone polyadenylation signal (bases 1069–1288); Co1E1 origin for growth in *Escherichia coli* (bases 1378–2051); thymidine kinase polyadenylation site (bases 2458–2187); neomycin resistance marker for stable selection in mammalian cells (bases 3421–2366, transcribed in counterclockwise direction); SV40 origin and promoter, for replication and simple vector rescue in cell lines expressing the large T-antigen (bases 3797–3456, counterclockwise); ampicillin-resistance gene for selection for selection in *E. coli* (4736–3876); and f1 origin (5000–5099).

Plasmid pDisplay was digested with BglII and SacII, and then ligated to DNA encoding H22 sc-Fv consisting of $V_L$-linker $V_H$ similarly digested. The plasmid pJG717 was obtained from ampicillin-resistant colonies obtained from transformed *E. coli*, and its structure was verified by appropriate restriction digests.

Example 2

Surface Expression of H22 in Murine Tumor Cells

Figure 2:
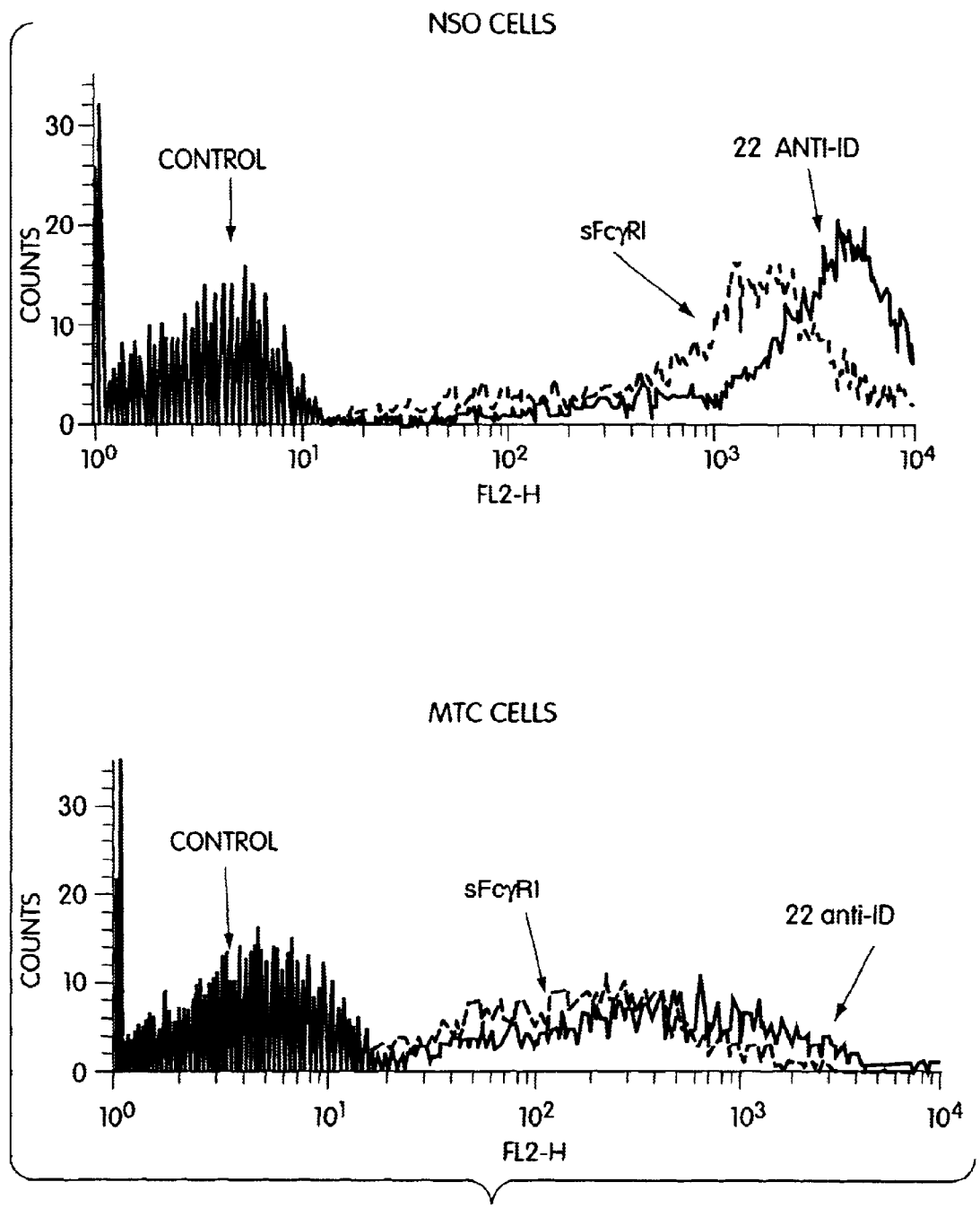
FIG. 2 is a FACS scan showing expression of H22-TM on the surface of transformed cells of mouse tumor cell lines. The top panel shows a FACS scan of NSO (mouse myeloma) cells carrying pJG717, and the bottom panel shows MTC (mouse thyroid medullary carcinoma) cells carrying pJG717.

Murine tumor cell lines, 653 and NSO (ATCC), were transformed with the H22-TM vector pJG717 (SEQ ID NO:1), and each cell line was established to have stable expression of the H22-TM fusion protein on cell surfaces as confirmed by flow cytometry using a soluble rabbit anti-H22 antibody, and with a soluble form of FcγRI (see FIG. 2). Untransformed 653 and NSO cells were used as controls. Cells were incubated with soluble rabbit anti-H22 antibody for 60 min. at 4° C. After washing the cells, antibody bound to cells was detected by a donkey anti-rabbit IgG-phycoerytherin probe. The transformed cells showed a significant shift in fluorescence when incubated with anti-H22 antibodies. These transformed cells were specifically lysed with G-CSF/IFN-γ treated granulocytes. Only the transformed cells were lysed by the effector cells and only the H22 F(ab')$_2$ fragments were able to inhibit the lysis of the transformed cells.

These results demonstrate that tumor cells can be transformed to express an anti-FcγR binding component, such as a single chain fragment of H22, on the surface of the cell (e.g., as a transmembrane fusion protein), thereby enabling the tumor cell to bind to soluble FcγRI.

Example 3

Surface Expression of H22 sFv Engages Effector Cells and Triggers FcγRI Effector Functions The following studies were performed to demonstrate that expression of H22-TM by tumor cells can lead to the engagement of FcγRI on effector cells, such as monocytes and activated granulocytes, thereby initiating FcγRI-dependent effector functions, such as cell lysis (e.g., ADCC), phagocytosis and cytokine secretion.

ADCC of H22-TM Transformed Cells by Activated Granulocytes

Chromium-labeled target murine tumor cells (NSO and 653) were transformed with pJG717 encoding the H22-TM fusion as described in Example 1 to act as target cells for cytokine activated granulocytes. These transformed cell lines were desginated as NSO-22TM and 553-22TM, respectively. ADCC was measured using a chromium release assay.

Figure 3:
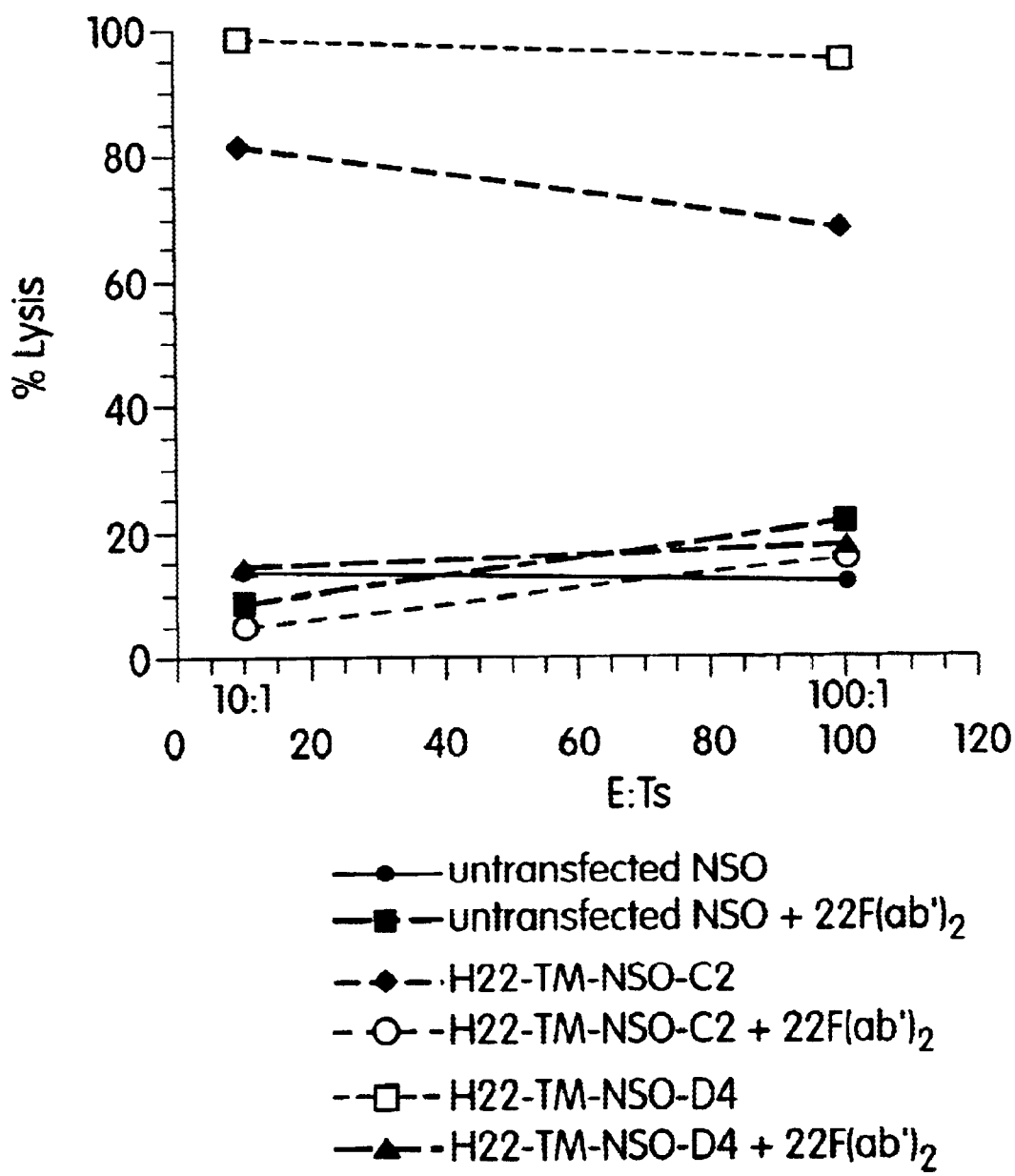
FIG. 3 is a graph showing H22-TM directed cytotoxicity as percent lysis of chromium-labeled target NSO cells transformed with pJG717, granulocyte-colony stimulating factor (G-CSF)-treated granulocytes as the effector cells, at varying effector:target ratios.

In particular, granulocytes were purified from normal whole blood and cultured overnight with G-CSF and IFN-γ. The effector cells were combined with $^{51}$Cr-labeled untransfected myeloma cells, 653-22TM cells, or NSO-22TM cells at an effector to target ratio of 50:1. H22 F(ab')$_2$ or A77F (ab')$_2$ was added in access to demonstrate specific blocking of the ADCC. Cytotoxicity was calculated by the formula: % lysis=(experimental CPM−target leak CPM/detergent lysis CPM−target leak CPM)×100%. Specific lysis was measured by % lysis with antibody−% lysis without antibody. Assays were performed in triplicate. The results for the NSO-22TM cells are shown in FIG. 3. The results for the 653-22TM cells are shown in FIG. 5.

Figure 5:
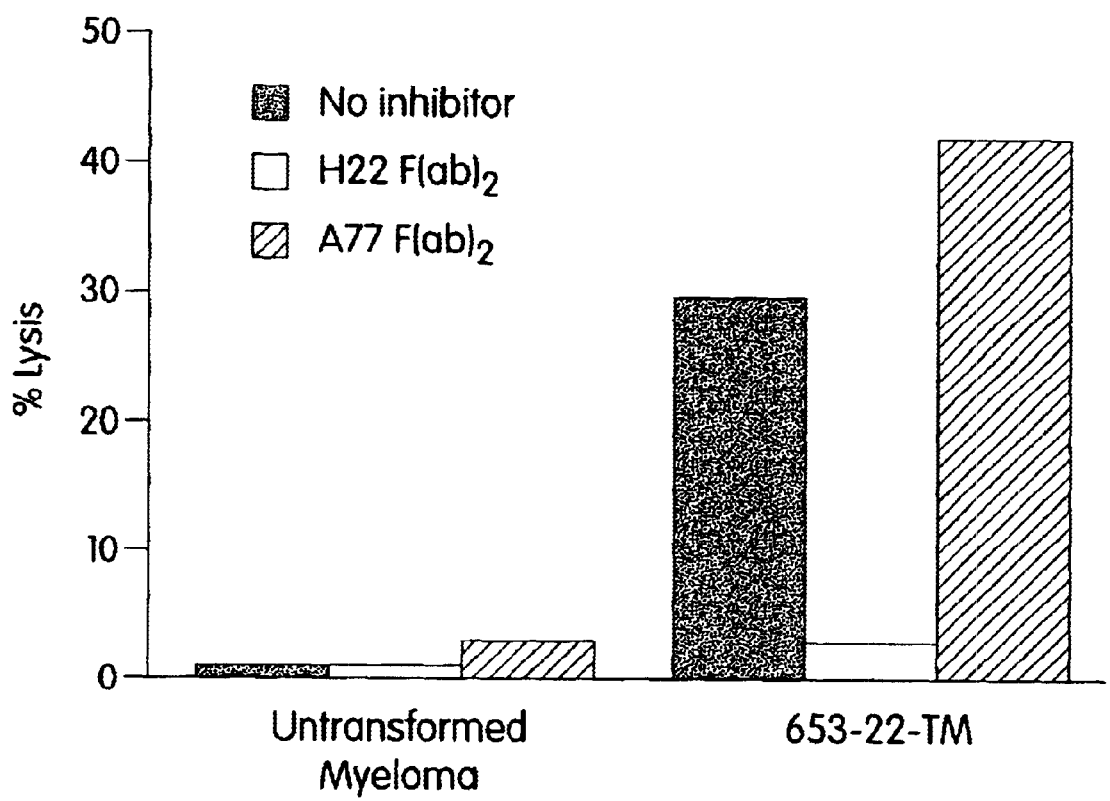
FIG. 5 is a graph showing ADCC of H22-TM expressing 653 myeloma cells by activated Granulocytes. Granulocytes were purified from normal whole blood and cultured overnight with G-CSF and IFN-γ. The effector cells were combined with $^{51}$Cr-labeled untransfected myeloma cells or 653-22TM cells at an effector to target ratio of 50:1. H22 F(ab')$_2$ or A77F(ab')$_2$ was added in access to demonstrate specific blocking of the ADCC. Results are shown as % lysis of H22-TM expressing 653 myeloma cells.

As shown in FIGS. 3 and 5, only those cells which expressed the H22-TM were killed by the granulocytes. Further, this activity was substantially or completely blocked by addition of soluble H22 F(ab')$_2$ antibody fragments. Untransformed control cells that did not express H22-TM were not lysed.

These data demonstrate that anti-FcγRI antibody determinants (e.g., sFv H22) can be expressed on the surface of tumor cells so the cells, when in the presence of activated granulocytes, engage and activate FcγRI resulting in specific lysis of the tumor cells. Furthermore, the lysis of 653-H22-TM cells could be specifically inhibited by addition of excess H22 F(ab')$_2$ fragments that bind to FcγRI, but not by A77F(ab')$_2$ fragments that bind to FcαR.

ADCC of H22-TM Transformed Cells by Monocytes

Chromium-labeled target murine myeloma 653 cells were transformed with pJG717 encoding the H22-TM fusion as described in Example 1 to act as target cells for macrophages. As in the previously described experiments, ADCC was measured using a chromium release assay.

In particular, monocytes were purified from normal human donors and differentiated into macrophages in the presence of IFN-γ. The effector cells were combined with $^{51}$Cr-labelled untransfected myeloma cells or $^{51}$Cr-labelled 653-22TM cells at an effector to target ration of 30:1 and incubated for 3.5 hours. H22 F(ab')$_2$ or A77F(ab')$_2$ was added in excess to demonstrate specific blocking of the ADCC.

Figure 6:
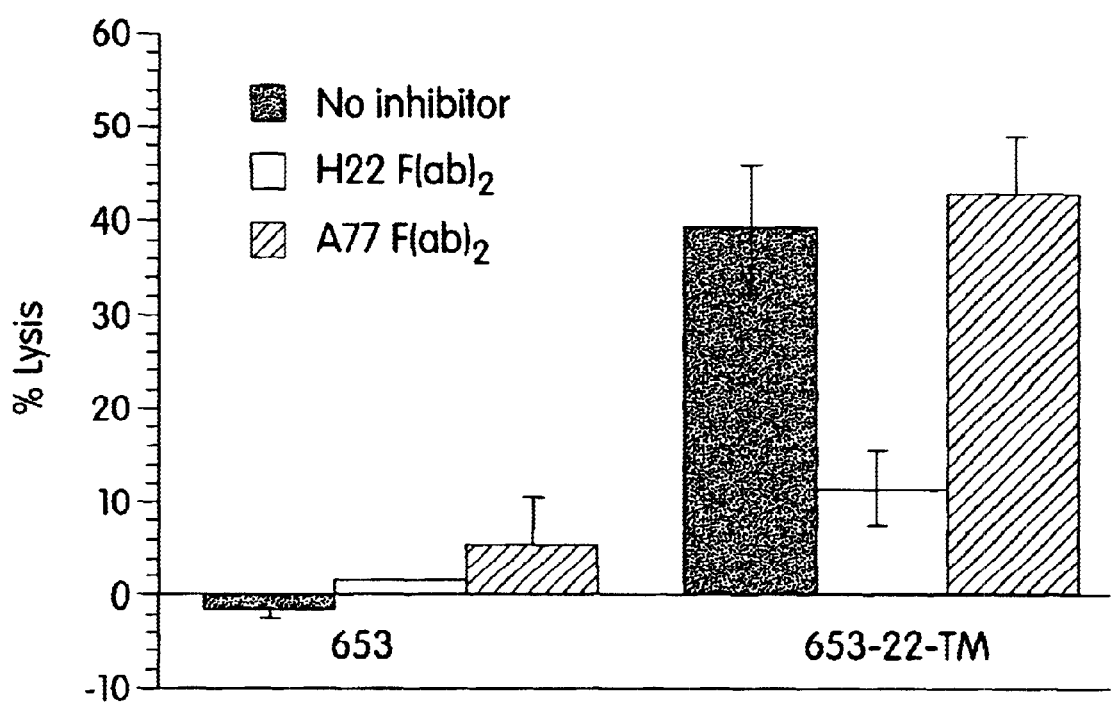
FIG. 6 is a graph showing ADCC of H22-TM expressing 653 myeloma cells by human macrophages. Monocytes were purified from normal donors and differentiated into macrophages in the presence of IFN-γ. The effector cells were combined with $^{51}$Cr-labelled untransfected myeloma cells or 653-22TM cells at an effector to target ration of 30:1 and incubated for 3.5 hours. H22 F(ab')$_2$ or A77F(ab')$_2$ was added in excess to demonstrate specific blocking of the ADCC. Results are shown as % lysis of H22-TM expressing 653 myeloma cells.

As shown in FIG. 6, when 653-22TM verses untransformed 653 myeloma cells were incubated alone with effector cells, only the 653-22TM cells were killed by the granulocytes. Further, this activity was substantially blocked by addition of soluble H22 F(ab')$_2$ antibody fragments.

These data demonstrate that anti-FcγRI antibody determinants (e.g., sFv H22) can be expressed on the surface of tumor cells so the cells, when in the presence of macrophages, engage and activate FcγRI resulting in specific lysis of the tumor cells. Furthermore, the lysis of 653-H22-TM cells could be specifically inhibited by addition of excess H22 F(ab')$_2$ fragments that bind to FcγRI, but not by A77F(ab')$_2$ fragments that bind to FcαR.

Phagocytosis of H22-TM Transformed Cells

A murine carcinoma cell line (MTC) was transformed with the H22-TM vector pJG717, and cell lines were established that have stable expression of the fusion protein on their plasma membrane as described in Example 1.

The functional expression of the H22-TM was demonstrated by enhanced phagocytosis of the two H22-TM expressing cells liens (MTC-22-A1, and MTC-22-A4) as compared to non-transformed MTC cells. In particular, phagocytosis was evaluated by a two-color flow cytometry assay, in which the target cells were labeled with a red fluorescent dye, and the effector cells were labeled with a green fluorescent dye. Thus, when macrophage engulfed the target cells, the macrophages had both green and red fluorescence.

Briefly, macrophages were cultured from monocytes in media containing M-CSF and IFN-γ. MTC cells were labeled with PKH-26 dye (Sigma) and cultured with macrophages in 24 well plated for 18 hours. The macrophages were stained with CD14-FITC before analysis of samples with a FACScan. The % phagocytosis was determined by the formula: (number of dual positive cells)/(total number of red cells)×100%. The effector to target ratio was 20:1.

Figure 7:
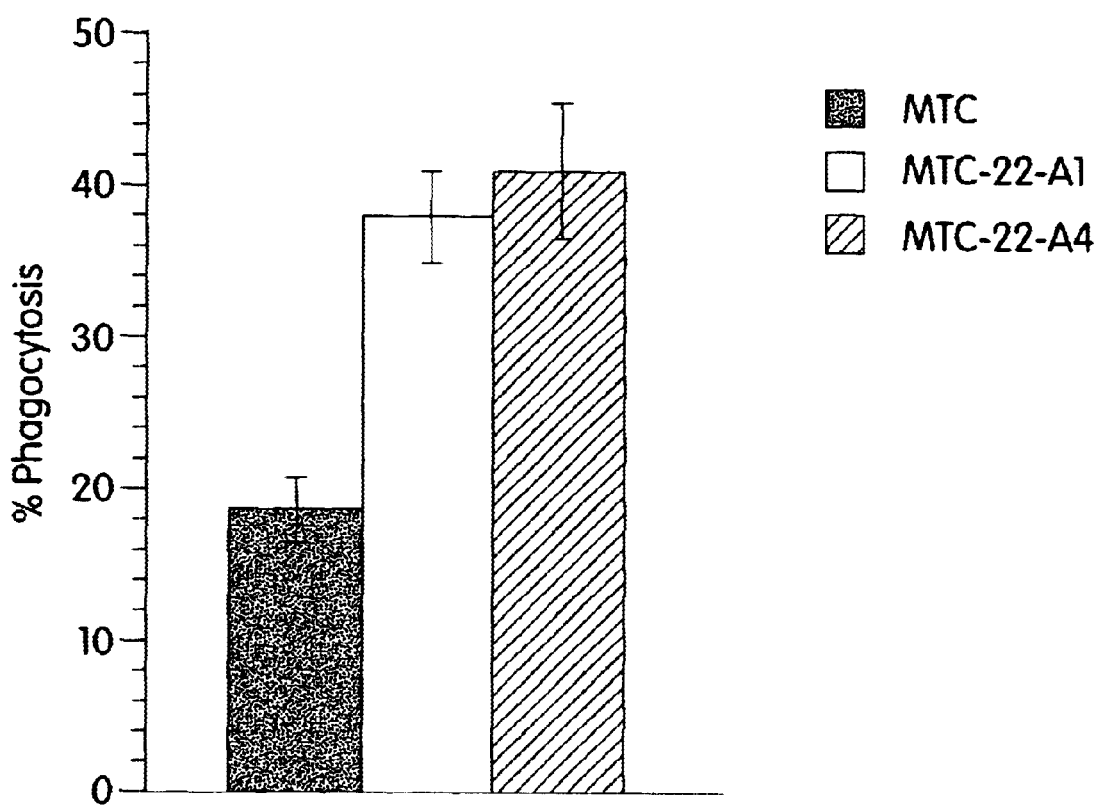
FIG. 7 is a graph showing phagocytosis of H22-TM expressing murine carcinoma cells (MTC) by human macrophages. Phagocytosis was evaluated by a two-color flow cytometry assay. Macrophages were cultured from monocytes in media containing M-CSF and IFN-γ. MTC cells were labeled with PKH-26 dye (Sigma) and cultured with macrophages in 24 well plated for 18 hours. The macrophages were stained with CD 14-FITC before analysis of samples with a FACScan. The % phagocytosis was determined by the formula: (number of dual positive cells)/(total number of red cells)×100%. The effector to target ratio was 20:1.

The results are shown in FIG. 7 which shows a significantly higher percentage of phagocytosis for transformed tumor cells (MTC-22-A1 and MTC-22-A4) compared to untransformed tumor cells (MTC). This demonstrates that transformation of tumor cells to express H22-TM substantially increases phagocytosis of the tumor cells by effector cells.

Induction of Cytokines by H22-TM Transformed Cells

A murine myeloma cell line (653) was transformed with the H22-TM vector pJG717, and cells lines were established that have stable expression of the fusion protein on their plasma membrane as described in Example 1. The functional expression of the H22-TM was demonstrated by eliciting the secretion of specific cytokine from effector cells as compared to non-transformed 653 cells. For example, the 653-22TM cell showed a specific induction of IL-1β, TNF-α, and IL-6 cytokines.

In particular, monocytes were purified from normal whole blood and allowed to adhere to plastic tissue culture plates. The moncytes were con-cultured with 653 cells or 653-22TM cells at an effector to target ratio of 5:1. Media was removed from the cultures at 0, 4, and 21 hours and measured for the presence of cytokines by commercially available kits.

Figure 8:
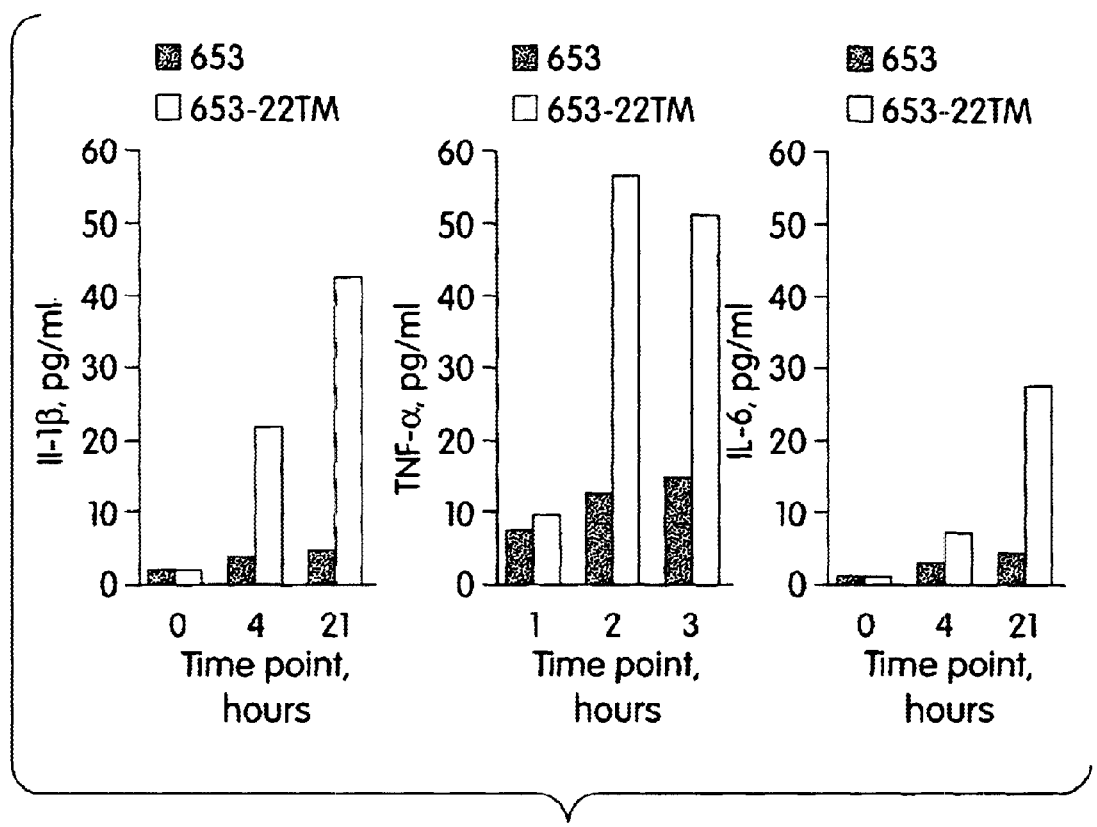
FIG. 8 is a graph showing induction of cytokines by H22-TM expressing murine myeloma cells (653). Monocytes were purified from normal whole human blood and allowed to adhere to plastic tissue culture plates. The monocytes were co-cultured with 653 cells or H22-Tm expressing 653 cells (653-22TM) at an effector to target ratio of 5:1. Media was removed from the cultures at 0, 4, and 21 hours and measured for the presence of cytokines by commercially available kits.

The results are shown in FIG. 8 which shows that 653-22TM cells were able to specifically induce IL-1β, TNF-α, and IL-6 cytokines. This demonstrates that transformation of tumor cells to express H22-TM causes the specific induction of cytokines.

Example 4

Targeting Antigen Presenting Cells to Tumors Expressing Antibody for FcγR

Transgenic mice expressing FcγRI can be used to evaluate the anti-tumor and antigen presentation capacity of the H22-TM vector. Tumor cells that express selected tumor-specific antigens can be transformed with vectors such as pJG717, and expression of the H22-TM will efficiently target these cells to antigen presenting cells (e.g., dendritic cells, monocytes and macrophages).

The antigen presenting cells can then phagocytose the H22-bearing cells through binding of FcγRI, and initiate an immune reaction specific to the antigens present, by expressing peptides derived from proteolytic cleavage of the tumor antigen, displayed on MHC molecules. In this manner, specific immunity against cells bearing such tumor antigens can be achieved. This can be done in vivo in patients or, alternatively in transgenic animals, such as transgenic mice expressing human FcγRI.

Example 5

Irradiation of Genetically Modified Cells ex vivo Prior to Administration to a Subject Cells expressing a tumor or a pathogen antigen can be engineered ex vivo to express H22-TM or a similar construct that binds an FcR, and can then be administered to a subject to generate a specific immune response. For this application the engineered cells that are "redirected" to bind an FcR can be irradiated prior to administration, to reduce or eliminate growth of the transformed cells in the patient (e.g., to ensure less than about 10% survival of the irradiated cells).

Example 6

Surface Expression of A77 sFv on Murine Myeloma Cells

Figure 9:
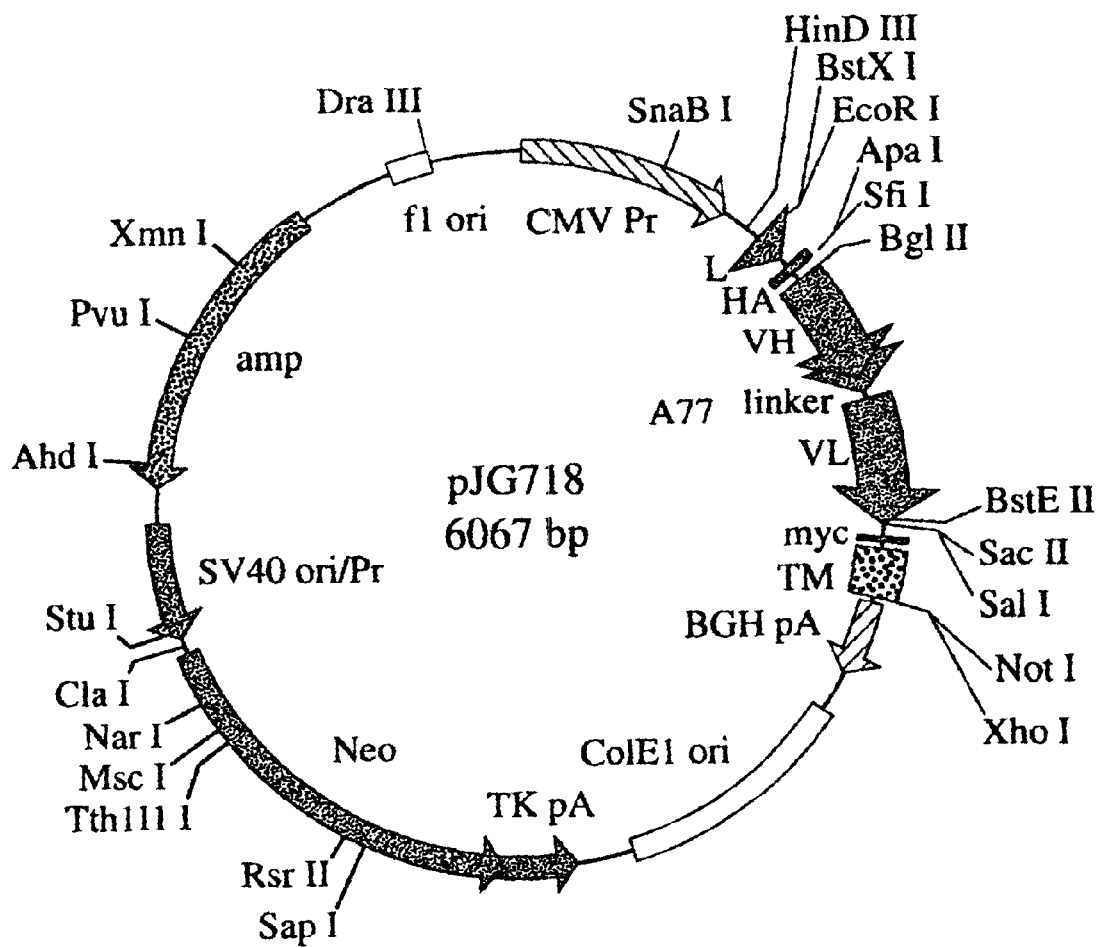
FIG. 9 is a map of the expression vector pJG718 encoding a fusion protein made up of the platelet derived growth factor receptor transmembrane domain (TM) and a single chain Fv fragment of anti-FcαR antibody A77. This fusion protein is referred to as A77-TM. The genetic regulatory control elements shown on the map correspond to those shown in FIG. 1.
Figure 11A:
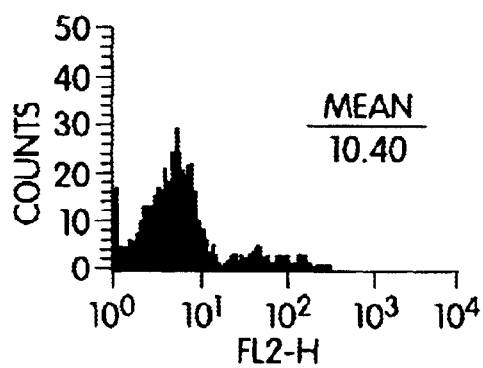
FIG. 11 is a FACS scan showing expression of A77-TM on the surface of transformed myeloma cells. The NS0-A77-TM transformed cell line (77-D6) was incubated with soluble FcαR (5 µg/ml) for 90 min. at 4° C. After washing the cells, IgA was added (20 µg/ml) was added for 90 min. at 4° C. The cells were washed again, and the IgA bound to cells was detected by a goat anti-human IgA-phycoerytherin probe. Panel A shows cells reacting only with probe, Panel B shows cells reacting with soluble FcαR and probe, Panel C shows cells reacting with IgA and probe, and Panel D shows cells reacting with soluble FcαR and IgA and probe.
Figure 11B:
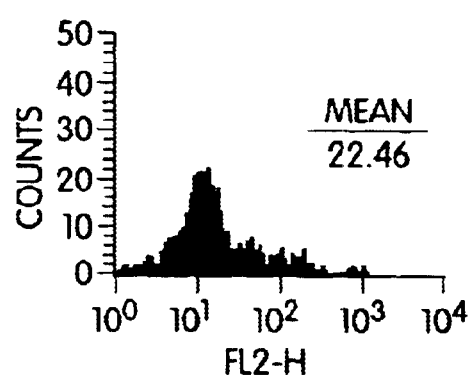
Figure 11C:
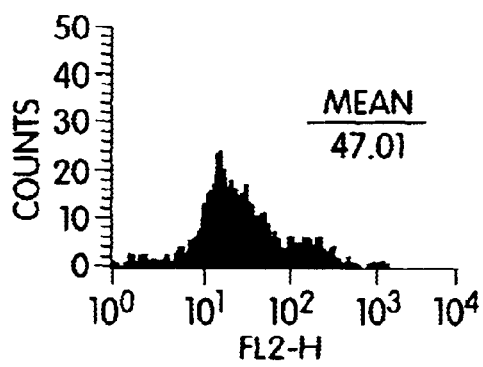
Figure 11D:
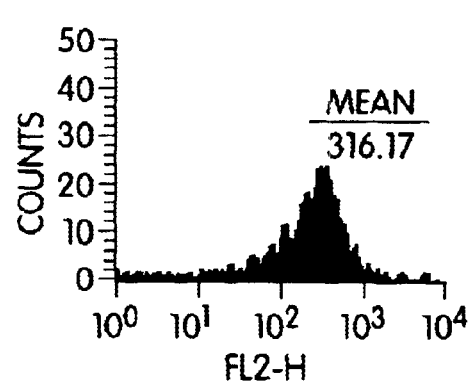

Murine myeloma cells (NSO) were transformed with an expression vector referred to as pJG718 (FIG. 9) encoding a fusion protein similar H22-TM as described in Example 1, except that the single chain anti-FcγRI portion (sFv H22) was replaced by a single chain anti-FcαR portion from antibody A77 (sFv A77). This fusion protein is referred to as A77-TM.

Cell lines were established that have stable expression of the fusion protein on their plasma membrane. As with H22-TM in Example 2, functional expression of the A77-TM in NSO cells was demonstrated by flow cytometry. In particular, the NSO A77-TM transformed cell line (77-D6) was incubated with soluble FcαR (5 μg/ml) for 90 min. at 4° C. After washing the cells, IgA was added (20 μg/ml) was added for 90 min. at 4° C. Again, the cells were washed, and the IgA bound to cells was detected by a goat anti-human IgA-phycoerytherin probe.

The results are shown in FIG. 11 which shows that transformed NSO A77-TM cells exhibited a significant shift in fluorescence, but only when both soluble FcαR and IgA were added. Panel A shows that cells reacted only with probe, Panel B shows that cells reacted with soluble FcαR and probe, Panel C shows that cells reacted with IgA and probe, Panel D shows that cells reacted with soluble FcαR and IgA and probe. Overall, these results demonstrate that tumor cells transformed to express A77-TM can bind a soluble form of the FcαR, and the bound FcαR can still engage IgA molecules.

Equivalents

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

All patents and publications referred to herein are hereby incorporated by reference.

---

What is claimed is:

1. A cell transformed in vitro or ex vivo to express on its surface a component which binds to an Fc receptor of an effector cell, wherein the surface component is recombinantly expressed as a fusion protein comprising an Fc receptor binding protein and transmembrane protein having a transmembrane domain from platelet derived growth factor receptor.

2. The cell of claim 1 which is a mammalian cell.

3. The cell of claim 1 further comprising on its surface an antigen selected from the group consisting of a tumor antigen and a component of a pathogen.

4. The cell of claim 1 which is a tumor cell.

5. The cell of claim 3, wherein the tumor antigen is selected from the group consisting of HER-2/neu, TAG 72, carcinoembryonic antigen, and gastrin releasing peptide.

6. The cell of claim 1, which is transformed ex vivo to express the component which binds to the Fc receptor.

7. The cell of claim 1, wherein the Fc receptor is selected from the group consisting of an Fcγ receptor, an Fcα receptor, an Fcμ receptor, and an Fcε receptor.

8. The cell of claim 1, wherein the Fc receptor is selected from the group consisting, of FcγI, FcγII, and FcγIII.

9. A cell transformed in vitro or ex vivo to express a fusion protein comprising (a) an antibody or antibody fragment which binds to an Fc receptor of an effector cell, wherein the binding to the Fc receptor is not blocked by endogenous antibody and (b) a transmembrane protein having a transmembrane domain from platelet derived growth factor receptor.

10. The cell of claim 9, wherein the fragment is a single chain Fv fragment.

11. The cell of claim 9, wherein the antibody is selected from the group consisting of an IgA, an IgG and fragments thereof.

12. The cell of claim 9, wherein the antibody or antibody fragment which binds to the Fc receptor is produced recombinantly in the cell.

13. The cell of claim 11, wherein binding of the antibody to the Fc receptor is not blocked by IgA or IgG.

14. The cell of claim 12 wherein the component binds to an Fcγ receptor or an Fcα receptor.

15. The cell of claim 9, wherein the antibody is selected from the group consisting of antibody H22 having ATCC deposit number CRL 11,177, and antibody A77.

16. The cell of claim 4, wherein the fragment is a single chain Fv fragment of antibody H22 or A77.

17. The cell of claim 9, wherein the cell is lysed or in the presence of the effector cell.

18. The cell of claim 17, wherein the antibody fragment is a single chain Fv fragment of antibody H22 having ATCC deposit number CRL 11,177 or of antibody A77.

19. The cell of claim 17, which is a tumor cell transformed ex vivo to express the fusion protein.

20. An expression vector encoding a fusion protein comprising a portion which binds to an Fc receptor on an effector cell, wherein the binding to the Fc receptor is not blocked by endogenous antibody, and transmembrane protein having a transmembrane domain from platelet derived growth factor receptor.

21. The expression vector of claim 20, wherein the portion that binds to an Fc receptor comprises an antibody or an antigen binding fragment thereof.

22. The expression of claim 21, where the antibody is selected from the group consisting of humanized antibody H22 having ATCC deposit number CRL 11177, and antibody A77.

23. The expression vector of claim 21, wherein the antigen binding fragment is a single chain Fv fragment which binds to an Fcγ receptor or an Fcα receptor.

24. The expression vector of claim 20, wherein the Fc receptor is an Fcγ receptor or an Fcα receptor.

* * * * *

SEQUENCE LISTING

```
<160> NUMBER OF SEQ ID NOS: 4

<210> SEQ ID NO 1
<211> LENGTH: 1132
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (74)...(1129)

<400> SEQUENCE: 1
aagcttggta ccgagctcgg atccactagt aacggccgcc agtgtgctgg aattcggctt          60
ggggatatcc acc atg gag aca gac aca ctc ctg cta tgg gta ctg ctg           109
            Met Glu Thr Asp Thr Leu Leu Leu Trp Val Leu Leu
              1               5                  10
ctc tgg gtt cca ggt tcc act ggt gac tat cca tat gat gtt cca gat           157
Leu Trp Val Pro Gly Ser Thr Gly Asp Tyr Pro Tyr Asp Val Pro Asp
           15                  20                  25 tat gct ggg gcc cag ccg gcc aga tct gat atc cag ctg acc cag agc           205
Tyr Ala Gly Ala Gln Pro Ala Arg Ser Asp Ile Gln Leu Thr Gln Ser
```

```
                30                    35                    40
cca agc agc ctg agc gcc agc gtg ggt gac aga gtg acc atc acc tgt       253
Pro Ser Ser Leu Ser Ala Ser Val Gly Asp Arg Val Thr Ile Thr Cys
 45                  50                  55                  60 aag tcc agt caa agt gtt tta tac agt tca aat cag aag aac tac ttg       301
Lys Ser Ser Gln Ser Val Leu Tyr Ser Ser Asn Gln Lys Asn Tyr Leu
                 65                  70                  75 gcc tgg tac cag cag aag cca ggt aag gct cca aag ctg ctg atc tac       349
Ala Trp Tyr Gln Gln Lys Pro Gly Lys Ala Pro Lys Leu Leu Ile Tyr
                     80                  85                  90 tgg gca tcc act agg gaa tct ggt gtg cca agc aga ttc agc ggt agc       397
Trp Ala Ser Thr Arg Glu Ser Gly Val Pro Ser Arg Phe Ser Gly Ser
             95                 100                 105 ggt agc ggt acc gac ttc acc ttc acc atc agc agc ctc cag cca gag       445
Gly Ser Gly Thr Asp Phe Thr Phe Thr Ile Ser Ser Leu Gln Pro Glu
    110                 115                 120 gac atc gcc acc tac tac tgc cat caa tac ctc tcc tcg tgg acg ttc       493
Asp Ile Ala Thr Tyr Tyr Cys His Gln Tyr Leu Ser Ser Trp Thr Phe
125                 130                 135                 140 ggc caa ggg acc aag gtg gaa atc aag agc tct ggc ggt ggc ggc tcc       541
Gly Gln Gly Thr Lys Val Glu Ile Lys Ser Ser Gly Gly Gly Gly Ser
                    145                 150                 155 gga ggt gga ggc agc gga ggg ggt gga tcc gag gtc caa ctg gtg gag       589
Gly Gly Gly Gly Ser Gly Gly Gly Gly Ser Glu Val Gln Leu Val Glu
                160                 165                 170 agc ggt gga ggt gtt gtg caa cct ggc cgg tcc ctg cgc ctg tcc tgc       637
Ser Gly Gly Gly Val Val Gln Pro Gly Arg Ser Leu Arg Leu Ser Cys
            175                 180                 185 tcc tcg tct ggc ttc att ttc agt gac aat tac atg tat tgg gtg aga       685
Ser Ser Ser Gly Phe Ile Phe Ser Asp Asn Tyr Met Tyr Trp Val Arg
        190                 195                 200 cag gca cct gga aaa ggt ctt gag tgg gtt gca acc att agt gat ggt       733
Gln Ala Pro Gly Lys Gly Leu Glu Trp Val Ala Thr Ile Ser Asp Gly
205                 210                 215                 220 ggt agt tac acc tac tat cca gac agt gtg aag gga aga ttt aca ata       781
Gly Ser Tyr Thr Tyr Tyr Pro Asp Ser Val Lys Gly Arg Phe Thr Ile
                225                 230                 235 tcg aga gac aac agc aag aac aca ttg ttc ctg caa atg gac agc ctg       829
Ser Arg Asp Asn Ser Lys Asn Thr Leu Phe Leu Gln Met Asp Ser Leu
                240                 245                 250 aga ccc gaa gac acc ggg gtc tat ttt tgt gca aga ggc tac tat agg       877
Arg Pro Glu Asp Thr Gly Val Tyr Phe Cys Ala Arg Gly Tyr Tyr Arg
            255                 260                 265 tac gag ggg gct atg gac tac tgg ggc caa ggg acc ccg gtc acc gtc       925
Tyr Glu Gly Ala Met Asp Tyr Trp Gly Gln Gly Thr Pro Val Thr Val
        270                 275                 280 tcc tca ccg cgg ctg cag gtc gac gaa caa aaa ctc atc tca gaa gag       973
Ser Ser Pro Arg Leu Gln Val Asp Glu Gln Lys Leu Ile Ser Glu Glu
285                 290                 295                 300 gat ctg aat gct gtg ggc cag gac acg cag gag gtc atc gtg gtg cca      1021
Asp Leu Asn Ala Val Gly Gln Asp Thr Gln Glu Val Ile Val Val Pro
                305                 310                 315 cac tcc ttg ccc ttt aag gtg gtg gtg atc tca gcc atc ctg gcc ctg      1069
His Ser Leu Pro Phe Lys Val Val Val Ile Ser Ala Ile Leu Ala Leu
                320                 325                 330 gtg gtg ctc acc atc atc tcc ctt atc atc ctc atc atg ctt tgg cag      1117
Val Val Leu Thr Ile Ile Ser Leu Ile Ile Leu Ile Met Leu Trp Gln
            335                 340                 345 aag aag cca cgt tag                                                  1132
```

```
Lys Lys Pro Arg
        350

<210> SEQ ID NO 2
<211> LENGTH: 352
<212> TYPE: PRT
<213> ORGANISM: Artificial Sequence
<220> FEATURE:
<223> OTHER INFORMATION: Synthetic construct

<400> SEQUENCE: 2

Met Glu Thr Asp Thr Leu Leu Leu Trp Val Leu Leu Leu Trp Val Pro
 1               5                  10                  15

Gly Ser Thr Gly Asp Tyr Pro Tyr Asp Val Pro Asp Tyr Ala Gly Ala
            20                  25                  30

Gln Pro Ala Arg Ser Asp Ile Gln Leu Thr Gln Ser Pro Ser Ser Leu
        35                  40                  45

Ser Ala Ser Val Gly Asp Arg Val Thr Ile Thr Cys Lys Ser Ser Gln
 50                  55                  60

Ser Val Leu Tyr Ser Ser Asn Gln Lys Asn Tyr Leu Ala Trp Tyr Gln
 65                  70                  75                  80

Gln Lys Pro Gly Lys Ala Pro Lys Leu Leu Ile Tyr Trp Ala Ser Thr
                85                  90                  95

Arg Glu Ser Gly Val Pro Ser Arg Phe Ser Gly Ser Gly Ser Gly Thr
            100                 105                 110

Asp Phe Thr Phe Thr Ile Ser Ser Leu Gln Pro Glu Asp Ile Ala Thr
        115                 120                 125

Tyr Tyr Cys His Gln Tyr Leu Ser Ser Trp Thr Phe Gly Gln Gly Thr
130                 135                 140

Lys Val Glu Ile Lys Ser Gly Gly Gly Gly Ser Gly Gly Gly Gly
145                 150                 155                 160

Ser Gly Gly Gly Gly Ser Glu Val Gln Leu Val Glu Ser Gly Gly Gly
                165                 170                 175

Val Val Gln Pro Gly Arg Ser Leu Arg Leu Ser Cys Ser Ser Ser Gly
            180                 185                 190

Phe Ile Phe Ser Asp Asn Tyr Met Tyr Trp Val Arg Gln Ala Pro Gly
        195                 200                 205

Lys Gly Leu Glu Trp Val Ala Thr Ile Ser Asp Gly Gly Ser Tyr Thr
210                 215                 220

Tyr Tyr Pro Asp Ser Val Lys Gly Arg Phe Thr Ile Ser Arg Asp Asn
225                 230                 235                 240

Ser Lys Asn Thr Leu Phe Leu Gln Met Asp Ser Leu Arg Pro Glu Asp
                245                 250                 255

Thr Gly Val Tyr Phe Cys Ala Arg Gly Tyr Arg Tyr Glu Gly Ala
            260                 265                 270

Met Asp Tyr Trp Gly Gln Gly Thr Pro Val Thr Val Ser Ser Pro Arg
        275                 280                 285

Leu Gln Val Asp Glu Gln Lys Leu Ile Ser Glu Glu Asp Leu Asn Ala
290                 295                 300

Val Gly Gln Asp Thr Gln Glu Val Ile Val Pro His Ser Leu Pro
305                 310                 315                 320

Phe Lys Val Val Val Ile Ser Ala Ile Leu Ala Leu Val Leu Thr
                325                 330                 335

Ile Ile Ser Leu Ile Ile Leu Ile Met Leu Trp Gln Lys Lys Pro Arg
            340                 345                 350
```

-continued

```
<210> SEQ ID NO 3
<211> LENGTH: 1135
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (74)...(1132)

<400> SEQUENCE: 3
aagcttggta ccgagctcgg atccactagt aacggccgcc agtgtgctgg aattcggctt      60 gggatatcc acc atg gag aca gac aca ctc ctg cta tgg gta ctg ctg         109
            Met Glu Thr Asp Thr Leu Leu Leu Trp Val Leu Leu
              1               5                  10 ctc tgg gtt cca ggt tcc act ggt gac tat cca tat gat gtt cca gat       157
Leu Trp Val Pro Gly Ser Thr Gly Asp Tyr Pro Tyr Asp Val Pro Asp
         15                  20                  25 tat gct ggg gcc cag ccg gcc aga tct gag atc cag ctg cag cag act       205
Tyr Ala Gly Ala Gln Pro Ala Arg Ser Glu Ile Gln Leu Gln Gln Thr
 30                  35                  40 gga cct gag ctg gtg aag cct ggg gct tca gtg aag ata tcc tgc aag       253
Gly Pro Glu Leu Val Lys Pro Gly Ala Ser Val Lys Ile Ser Cys Lys
 45                  50                  55                  60 gct tct ggt tat tca ttc act gac tac atc ata ttt tgg gtg aag cag       301
Ala Ser Gly Tyr Ser Phe Thr Asp Tyr Ile Ile Phe Trp Val Lys Gln
                 65                  70                  75 agc cat gga aag agc ctt gag tgg act gga aat aat aat cct tac tat       349
Ser His Gly Lys Ser Leu Glu Trp Thr Gly Asn Asn Asn Pro Tyr Tyr
             80                  85                  90 ggt agt act agc tac aat ctg aag ttc aag ggc aag gcc aca ttg act       397
Gly Ser Thr Ser Tyr Asn Leu Lys Phe Lys Gly Lys Ala Thr Leu Thr
         95                 100                 105 gta gac aaa tct tcc agc aca gcc tac atg cag ctc aac agt ctg aca       445
Val Asp Lys Ser Ser Ser Thr Ala Tyr Met Gln Leu Asn Ser Leu Thr
    110                 115                 120 tct gag gac tct gca gtc tat tac tgt gta aga gga gtt tat tac tac       493
Ser Glu Asp Ser Ala Val Tyr Tyr Cys Val Arg Gly Val Tyr Tyr Tyr
125                 130                 135                 140 ggt agt agc tac gag gcg ttt cct tac tgg ggc caa ggg act ctg gtc       541
Gly Ser Ser Tyr Glu Ala Phe Pro Tyr Trp Gly Gln Gly Thr Leu Val
                145                 150                 155 act gtc tct gca gga ggt ggc ggc tcc gga gga ggt ggc agc gga ggg       589
Thr Val Ser Ala Gly Gly Gly Gly Ser Gly Gly Gly Gly Ser Gly Gly
            160                 165                 170 ggc gga tcc gat gtt gtg atg acc cag act cca ctc act ttg tcg att       637
Gly Gly Ser Asp Val Val Met Thr Gln Thr Pro Leu Thr Leu Ser Ile
        175                 180                 185 acc att gga caa cca gcc tcc atc tct tgc aag tca agt cag agc ctc       685
Thr Ile Gly Gln Pro Ala Ser Ile Ser Cys Lys Ser Ser Gln Ser Leu
    190                 195                 200 tta gat agt gat gga aag aca tat ttg aat tgg ttg tta cag agg cca       733
Leu Asp Ser Asp Gly Lys Thr Tyr Leu Asn Trp Leu Leu Gln Arg Pro
205                 210                 215                 220 ggc cag tct cca acg cgc cta atc tat ctg gtg tct aaa ctg gac tct       781
Gly Gln Ser Pro Thr Arg Leu Ile Tyr Leu Val Ser Lys Leu Asp Ser
                225                 230                 235 gga gtc cct gac agg ttc act ggc agt gga tca ggg aca gat ttc aca       829
Gly Val Pro Asp Arg Phe Thr Gly Ser Gly Ser Gly Thr Asp Phe Thr
            240                 245                 250
```

```
ctg aaa atc agc aga gtg gag gct gag gat ttg gga att tat tat tgc       877
Leu Lys Ile Ser Arg Val Glu Ala Glu Asp Leu Gly Ile Tyr Tyr Cys
        255                 260                 265 tgg caa ggt gca cat ttt cct cag acg ttc ggt gga ggc acc aag ctg       925
Trp Gln Gly Ala His Phe Pro Gln Thr Phe Gly Gly Gly Thr Lys Leu
270                 275                 280 gaa atc aaa ccg cgg ctg cag gtc gac gaa caa aaa ctc atc tca gaa       973
Glu Ile Lys Pro Arg Leu Gln Val Asp Glu Gln Lys Leu Ile Ser Glu
285                 290                 295                 300 gag gat ctg aat gct gtg ggc cag gac acg cag gag gtc atc gtg gtg      1021
Glu Asp Leu Asn Ala Val Gly Gln Asp Thr Gln Glu Val Ile Val Val
                305                 310                 315 cca cac tcc ttg ccc ttt aag gtg gtg gtg atc tca gcc atc ctg gcc      1069
Pro His Ser Leu Pro Phe Lys Val Val Val Ile Ser Ala Ile Leu Ala
            320                 325                 330 ctg gtg gtg ctc acc atc atc tcc ctt atc atc ctc atc atg ctt tgg      1117
Leu Val Val Leu Thr Ile Ile Ser Leu Ile Ile Leu Ile Met Leu Trp
        335                 340                 345 cag aag aag cca cgt tag                                               1135
Gln Lys Lys Pro Arg
    350
```

<210> SEQ ID NO 4
<211> LENGTH: 353
<212> TYPE: PRT
<213> ORGANISM: Artificial Sequence
<220> FEATURE:
<223> OTHER INFORMATION: Synthetic construct

<400> SEQUENCE: 4

```
Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala Gly Ala
            20                  25                  30

Gln Pro Ala Arg Ser Glu Ile Gln Leu Gln Gln Thr Gly Pro Glu Leu
        35                  40                  45

Val Lys Pro Gly Ala Ser Val Lys Ile Ser Cys Lys Ala Ser Gly Tyr
    50                  55                  60

Ser Phe Thr Asp Tyr Ile Ile Phe Trp Val Lys Gln Ser His Gly Lys
65                  70                  75                  80

Ser Leu Glu Trp Thr Gly Asn Asn Pro Tyr Tyr Gly Ser Thr Ser
                85                  90                  95

Tyr Asn Leu Lys Phe Lys Gly Lys Ala Thr Leu Thr Val Asp Lys Ser
            100                 105                 110

Ser Ser Thr Ala Tyr Met Gln Leu Asn Ser Leu Thr Ser Glu Asp Ser
        115                 120                 125

Ala Val Tyr Tyr Cys Val Arg Gly Val Tyr Tyr Gly Ser Ser Tyr
130                 135                 140

Glu Ala Phe Pro Tyr Trp Gly Gln Gly Thr Leu Val Thr Val Ser Ala
145                 150                 155                 160

Gly Gly Gly Gly Ser Gly Gly Gly Gly Ser Gly Gly Gly Gly Ser Asp
                165                 170                 175

Val Val Met Thr Gln Thr Pro Leu Thr Leu Ser Ile Thr Ile Gly Gln
            180                 185                 190

Pro Ala Ser Ile Ser Cys Lys Ser Ser Gln Ser Leu Leu Asp Ser Asp
        195                 200                 205

Gly Lys Thr Tyr Leu Asn Trp Leu Leu Gln Arg Pro Gly Gln Ser Pro
    210                 215                 220
```

-continued

```
Thr Arg Leu Ile Tyr Leu Val Ser Lys Leu Asp Ser Gly Val Pro Asp
225             230                 235                 240

Arg Phe Thr Gly Ser Gly Ser Gly Thr Asp Phe Thr Leu Lys Ile Ser
            245                 250                 255

Arg Val Glu Ala Glu Asp Leu Gly Ile Tyr Tyr Cys Trp Gln Gly Ala
            260                 265                 270

His Phe Pro Gln Thr Phe Gly Gly Gly Thr Lys Leu Glu Ile Lys Pro
        275                 280                 285

Arg Leu Gln Val Asp Glu Gln Lys Leu Ile Ser Glu Glu Asp Leu Asn
        290                 295                 300

Ala Val Gly Gln Asp Thr Gln Glu Val Ile Val Val Pro His Ser Leu
305             310                 315                 320

Pro Phe Lys Val Val Val Ile Ser Ala Ile Leu Ala Leu Val Val Leu
                325                 330                 335

Thr Ile Ile Ser Leu Ile Ile Leu Ile Met Leu Trp Gln Lys Lys Pro
            340                 345                 350

Arg
```